(12) United States Patent
Dobashi et al.

(10) Patent No.: US 12,414,819 B2
(45) Date of Patent: Sep. 16, 2025

(54) HYDROGEL CO-INJECTION AND REAL-TIME OPTO-ELECTROMAGNETIC MODIFICATION DEVICE FOR TUNABLE IN-VIVO DELIVERY

(71) Applicants: SUNNYBROOK RESEARCH INSTITUTE, Toronto (CA); RYERSON UNIVERSITY, Toronto (CA); THE UNIVERSITY OF BRITISH COLUMBIA, Vancouver (CA)

(72) Inventors: Yuta Dobashi, Toronto (CA); Jerry Ku, Toronto (CA); Joel Ramjist, Toronto (CA); Christopher Pasarikovski, Toronto (CA); Konrad Walus, Vancouver (CA); John Madden, Vancouver (CA); Victor Yang, North York (CA)

(73) Assignees: THE UNIVERSITY OF BRITISH COLUMBIA, Vancouver (CA); RYERSON UNIVERSITY, Toronto (CA); SUNNYBROOK RESEARCH INSTITUTE, Toronto (CA)

( * ) Notice: Subject to any disclaimer, the term of this patent is extended or adjusted under 35 U.S.C. 154(b) by 798 days.

(21) Appl. No.: 17/453,065

(22) Filed: Nov. 1, 2021

(65) Prior Publication Data
US 2022/0133408 A1 May 5, 2022

Related U.S. Application Data

(60) Provisional application No. 63/109,009, filed on Nov. 3, 2020.

(51) Int. Cl.
*A61B 18/24* (2006.01)
*A61B 18/00* (2006.01)
(Continued)

(52) U.S. Cl.
CPC ......... *A61B 18/24* (2013.01); *A61M 25/0026* (2013.01); *A61M 25/005* (2013.01);
(Continued)

(58) Field of Classification Search
CPC ............ A61B 18/24; A61B 2018/0016; A61B 17/12113; A61B 2017/12068;
(Continued)

(56) References Cited

U.S. PATENT DOCUMENTS

| 5,100,429 A | 3/1992 | Sinofsky et al. |
| 5,674,287 A | 10/1997 | Slepian |

(Continued)

FOREIGN PATENT DOCUMENTS

| EP | 3338820 A1 | 6/2018 |
| WO | 9508289 A2 | 3/1995 |
| WO | 2016185440 A1 | 11/2016 |

OTHER PUBLICATIONS

"Pioletti, et al., frontiers in Bioengineering and Biotechnology, Apr. 3, 2020, vol. 8-Article 261, pp. 1-13" (Year: 2020).*
(Continued)

*Primary Examiner* — Jennifer Pitrak McDonald
*Assistant Examiner* — Michael T. Holtzclaw

(57) ABSTRACT

Described herein are systems, devices and methods that enable dynamic modification of the physicochemical properties of a hydrogel during its in vivo formation and delivery by a catheter. In some example embodiments, an extended endoluminal hydrogel delivery device is employed for delivering a hydrogel within a given body cavity, such as within the lumen of a blood vessel. In some example embodiments, a hydrogel precursor, as a non-viscous liquid, is injected through an intravascular catheter and crosslinking of the hydrogel precursor is initiated within a distal region of the catheter. The crosslinking process is controlled, by a control (Continued)

means associated with a distal region of the catheter, to control or modify one or more properties of the hydrogel. The properties may be controlled such that a hydrogel is suitable to embolize the specific target or deliver drugs or other materials beneficial to the site.

25 Claims, 14 Drawing Sheets

(51) Int. Cl.
    *A61B 18/20*     (2006.01)
    *A61M 25/00*     (2006.01)

(52) U.S. Cl.
    CPC .............. *A61B 2018/0016* (2013.01); *A61B 2018/2065* (2013.01); *A61M 2025/0039* (2013.01); *A61M 2025/0057* (2013.01); *A61M 2205/3334* (2013.01)

(58) Field of Classification Search
    CPC .... A61B 17/12109; A61B 2017/00867; A61B 17/1219; A61M 25/0026; A61M 25/005; A61M 2025/0039; A61M 2025/0057; A61M 2205/3334; A61F 2/95
    USPC .......................................................... 606/15
    See application file for complete search history.

(56) References Cited

U.S. PATENT DOCUMENTS

| | | |
|---|---|---|
| 5,860,948 A | 1/1999 | Buscemi |
| 6,102,905 A * | 8/2000 | Baxter ..................... A61L 2/10 |
| | | 606/7 |
| 6,576,000 B2 | 6/2003 | Carrison |
| 6,689,148 B2 | 2/2004 | Sawhney et al. |
| 7,294,334 B1 | 11/2007 | Michal et al. |
| 7,653,432 B2 | 1/2010 | Doty |
| 7,955,365 B2 | 6/2011 | Doty |
| 9,220,761 B2 | 12/2015 | Barnett et al. |
| 9,907,906 B2 * | 3/2018 | Ordeig .............. A61M 5/16813 |
| 11,779,422 B2 * | 10/2023 | Zhao ..................... A61B 34/30 |
| | | 606/15 |
| 2002/0165582 A1 | 11/2002 | Porter |
| 2004/0230156 A1 | 11/2004 | Schreck et al. |
| 2005/0158272 A1 | 7/2005 | Whirley et al. |
| 2007/0225799 A1 | 9/2007 | Doty |
| 2008/0004686 A1 * | 1/2008 | Hunt ...................... A61L 31/14 |
| | | 606/14 |
| 2008/0033341 A1 * | 2/2008 | Grad ..................... A61M 25/00 |
| | | 604/20 |
| 2008/0132936 A1 * | 6/2008 | Sawhney ......... A61B 17/12099 |
| | | 606/192 |
| 2008/0154234 A1 * | 6/2008 | Behravesh ....... A61B 17/00491 |
| | | 604/506 |
| 2015/0305892 A1 | 10/2015 | Hossainy et al. |
| 2016/0256705 A1 * | 9/2016 | Webler, Jr. ......... A61M 25/0084 |
| 2017/0274218 A1 * | 9/2017 | Schmocker ........... A61N 5/062 |
| 2018/0056086 A1 | 3/2018 | Harari |
| 2018/0140303 A1 | 5/2018 | Schmocker et al. |
| 2020/0237388 A1 | 7/2020 | Eisenfrats et al. |
| 2021/0260578 A1 * | 8/2021 | Shirwaiker .......... C12N 5/0062 |

OTHER PUBLICATIONS

"APC International, What is a Piezo Transducer?, 2024, pp. 1-12" (Year: 2024).*

"Rossky, et al., PNAS, Aug. 3, 2010, vol. 107, No. 31, pp. 13603-13607" (Year: 2010).*

* cited by examiner

HYDROGEL CO-INJECTION AND REAL-TIME OPTO-ELECTROMAGNETIC MODIFICATION DEVICE FOR TUNABLE IN-VIVO DELIVERY

CROSS-REFERENCE TO RELATED APPLICATIONS

This application claims priority to U.S. Provisional Patent Application No. 63/109,009 titled "HYDROGEL CO-INJECTION AND REAL-TIME OPTO-ELECTROMAGNETIC MODIFICATION DEVICE FOR TUNABLE IN-VIVO DELIVERY" and filed on Nov. 3, 2020, the entire contents of which is incorporated herein by reference.

BACKGROUND

The present disclosure relates to therapeutic endovascular catheters. In some aspects, the present disclosure relates to the use of catheters for therapeutic embolization procedures.

Minimally invasive endovascular treatments have greatly changed the clinical landscape of many conditions such as coronary artery diseases, strokes, hemorrhagic vessels, vascularized tumors, aneurysms, and arteriovenous malformations. In these treatments, a catheter is navigated through the body to the intended site, at which a multitude of interventions, such as thrombus retrieval, ablation, stent placement, and embolization can be performed.

Therapeutic embolization aims to cease the local blood flow in peripheral vasculature so as to combat hemorrhage or to shut down supply to malignant tissues. Therapeutic embolization can be performed as primary or adjunctive treatment for a variety of disorders, including aneurysms, arteriovenous malformations, tumors, hyperplastic conditions, or hemorrhagic vessels. Embolic agents available include detachable mechanical devices such as coils or stents, liquid agents, or particulate material.

A significant portion of the current clinical limitations, in terms of safety and efficacy, of therapeutic embolization relate to the limitations of the available embolic agents themselves, including material compaction/migration, disease recurrence, non target embolization, or toxicity. Furthermore, in addition to embolization, minimally invasive delivery of biologically relevant materials has been of high interest for drug deposition, cell therapies, tissue engineering, and other applications of the like.

SUMMARY

The present disclosure provides catheter systems capable of delivering or co-delivering hydrogels while simultaneously altering the chemical and physical properties to suit various purposes and for improved operational control. In some example embodiments, a hydrogel precursor, as a non-viscous liquid, is injected through an intravascular catheter and crosslinking of the hydrogel precursor is initiated within a distal region of the catheter. The cross-linking process is controlled, by a control means associated with a distal region of the catheter, to control or modify one or more properties of the hydrogel, examples of which include viscosity, mechanical moduli, conductivity, macromolecular permeability, and shape. The one or more properties are controlled such that a hydrogel is formed that is suitable to embolize the specific target or deliver drugs or other materials beneficial to the site.

As noted above, in some example embodiments, feedback is employed such that the properties of the hydrogel are controlled (e.g. altered) during crosslinking. Crosslinking may be performed, for example, with photo-crosslinking with or without adjunctive cross-linking measures, including ionic or thermal cross-linking.

In example implementations involving photo-crosslinking, the degree of photo-crosslinking may be controlled, for example, based on the optical irradiance and/or the rate of injection. Photo-crosslinking may be dynamically altered during injection by changing the laser power and the position of the optical source (e.g. an optical fiber) in relation to the catheter.

Some example embodiments employ multilumen geometries to facilitate coinjections and/or sequential injection for altering the macromorphological features. In some example embodiments, orthogonal modification methods may be performed based on secondary network crosslinking (other than photo-crosslinking) and/or the application of electromagnetic field for lemplating' the micromorphological features can be employed to work in concert with the modulated photo-crosslinking.

Accordingly, in one aspect, there is provided a system for controlled crosslinking and delivery of a hydrogel precursor within a bodily lumen, the system comprising:
  a catheter;
  flow means operably connectable to a proximal region of the catheter for delivering a hydrogel precursor into the catheter and flowing the hydrogel precursor within the catheter to a distal extrusion port within the catheter;
  a light source capable of emitting incident optical radiation suitable for crosslinking the hydrogel precursor;
  an optical fiber at least partially residing within the catheter, the optical fiber being configured to deliver the incident optical radiation emitted by the light source within the catheter such that the hydrogel precursor is illuminated by the incident optical radiation and is at least partially crosslinked by the incident optical radiation prior to and/or after being extruded through the distal extrusion port;
  a detector in optical communication with the optical fiber for detecting optical energy collected from the hydrogel precursor when the hydrogel precursor is illuminated by the incident optical radiation as the hydrogel precursor undergoes at least partial crosslinking; and
  control and processing circuity operably coupled to the detector and the light source, the control and processing circuity comprising at least one processor and associated memory, the memory comprising instructions executable by the at least one processor for performing instructions comprising:
  controlling crosslinking of the hydrogel precursor by the incident optical radiation according to feedback generated based on a signal obtained from the detector.

In some example implementations of the system, the catheter comprises a single-lumen distal reaction chamber extending from a location remote from a proximal end of the catheter to a distal end of the catheter for partially crosslinking the hydrogel precursor within the catheter before extruding the hydrogel precursor through the distal extrusion port into the bodily lumen; wherein a distal end of the optical fiber is longitudinally positionable within the single-lumen distal reaction chamber for controlling a volume of the hydrogel precursor that is irradiated by the incident optical radiation prior to being extruded through the distal extrusion port.

The single-lumen distal reaction chamber may reside distalward from a multilumen region of the catheter. The multilumen region of the catheter may comprise a conduit housed within the catheter, the multilumen region thereby comprising (i) an outer lumen formed between an outer sheath of the catheter and the conduit, and (ii) at least one inner lumen defined within the conduit, such that the single-lumen distal reaction chamber extends between a distal end of the multilumen region and the distal end of the catheter. A distal end of the conduit may be longitudinally positionable within the catheter for controlling a longitudinal extent of the single-lumen distal reaction chamber.

A first flow means may be configured to deliver a first hydrogel precursor to the inner lumen of the multilumen region, and a second flow means may be configured to deliver a second fluid to the outer lumen of the multilumen region. The inner lumen and the outer lumen may be coaxial. The control and processing circuity may be operably connected to the first flow means and the second flow means for controlling a flow rate of the first hydrogel precursor and the second fluid. The second fluid may be configured to provide a sheath flow around the first hydrogel precursor when the first hydrogel precursor emerges from the multilumen region. The second fluid may comprise a second hydrogel precursor.

In some example implementations of the system, the detector is configured to detect reflected optical energy that is responsively reflected by the hydrogel precursor when the hydrogel precursor is illuminated by the incident optical radiation as the hydrogel precursor undergoes at least partial crosslinking.

In some example implementations of the system, the detector is configured to detect emitted optical energy that is responsively emitted by the hydrogel precursor when the hydrogel precursor is illuminated by the incident optical radiation as the hydrogel precursor undergoes at least partial crosslinking. The detector may be configured to detect autofluorescence energy that is responsively emitted by the hydrogel precursor when the hydrogel precursor is illuminated by the incident optical radiation as the hydrogel precursor undergoes at least partial crosslinking. The detector may be configured to detect fluorescence energy that is responsively emitted by a fluorescent component of the hydrogel precursor when the hydrogel precursor is illuminated by the incident optical radiation as the hydrogel precursor undergoes at least partial crosslinking. The detector may be configured to detect fluorescence energy that is responsively emitted by a fluorescent component of the hydrogel precursor when the hydrogel precursor is illuminated by the incident optical radiation and the fluorescent component reaches a target site within the bodily lumen.

In some example implementations of the system, the detector is configured to detect one or more spectrally resolved optical signals. The detector may comprise a spectrometer.

In some example implementations of the system, the control and processing circuity is coupled to the flow means, and wherein the control and processing circuity is further configured to control the flow means according to the feedback generated based on the signal obtained from the detector.

In some example implementations of the system, the hydrogel precursor comprises an electrically alignable component capable of undergoing spatial alignment via an electric field, the system further comprising an electric field generator integrated with a distal region of the catheter, the electric field generator being configured to generate an applied electric field suitable for inducing spatial alignment of the electrically alignable component of the hydrogel precursor for generating anisotropy within the at least partially-crosslinked hydrogel precursor. The electric field generator may comprise an array of electrodes integrated with the distal region of the catheter.

In some example implementations of the system, the hydrogel precursor comprises a magnetically alignable component capable of undergoing spatial alignment via a magnetic field, the system further comprising a magnetic field generator integrated with a distal region of the catheter, the magnetic field generator being configured to generate an applied magnetic field suitable for inducing spatial alignment of the magnetically alignable component of the hydrogel precursor within the distal region for generating anisotropy within the at least partially-crosslinked hydrogel precursor. The magnetic field generator may comprise a coil integrated with the distal region of the catheter.

In some example implementations, the system further comprises an ultrasound generator integrated with a distal region of the catheter, the ultrasound generator being configured to generate an ultrasound field suitable for inducing spatial alignment of an acoustically alignable component of the hydrogel precursor within the distal region for generating anisotropy within the at least partially-crosslinked hydrogel precursor. The ultrasound generator may comprise a piezoelectric transducer integrated with the distal region of the catheter.

In some example implementations of the system, the optical fiber comprises a hydrophobic coating layer.

In another aspect, there is provided a system for controlled crosslinking and delivery of a hydrogel precursor within a bodily lumen, the system comprising:
 a catheter;
 flow means operably connectable to a proximal region of the catheter for delivering a hydrogel precursor into the catheter and flowing the hydrogel precursor within the catheter to a distal extrusion port within the catheter;
 a light source capable of emitting incident optical radiation suitable for crosslinking the hydrogel precursor; and
 an optical fiber at least partially residing within the catheter, the optical fiber being configured to deliver the incident optical radiation emitted by the light source within the catheter such that the hydrogel precursor is illuminated by the incident optical radiation and is at least partially crosslinked by the incident optical radiation prior to and/or after being extruded through the distal extrusion port;
 the catheter further comprising a single-lumen distal reaction chamber extending from a location remote from a proximal end of the catheter to a distal end of the catheter for partially crosslinking the hydrogel precursor before extruding the hydrogel precursor through the distal extrusion port into the bodily lumen;
 wherein a distal end of the optical fiber is longitudinally positionable within the single-lumen distal reaction chamber for controlling a volume of the hydrogel precursor that is illuminated by the incident optical radiation prior to being extruded through the distal extrusion port.

In some example implementations of the system, the single-lumen distal reaction chamber resides distalward from a multilumen region of the catheter.

The multilumen region of the catheter may comprise a conduit housed within the catheter, the multilumen region thereby comprising (i) an outer lumen formed between an outer sheath of the catheter and the conduit, and (ii) at least one inner lumen defined within the conduit, such that the single-lumen distal reaction chamber extends between a distal end of the multilumen region and the distal end of the catheter; and wherein a distal end of the conduit is longitudinally positionable within catheter for controlling a longitudinal extent of the single-lumen distal reaction chamber.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 8A and 8B show pre- and post-renal embolization (full casting of renal tree), respectively. FIG. 8C shows pre-hydrogel-injection common carotid artery injection showing filling of ascending pharyngeal artery (APA) into rete mirabile and filling of external carotid artery (ECA) vessels towards the face/jaw. FIG. 8D shows post-hydrogel-injection common carotid artery showing embolization of rete mirabile, APA, and ECA branches. No filling of contralateral rete and APA is observed.

FIG. 9A shows pre embolization of common femoral artery tree, while FIG. 9B shows 5 min following embolization (6 cc injected); internal iliac now occluded. FIGS. 9C and 9D respectively show the image of pre hydrogel injection distal subclavian artery and post hydrogel injection, with no filling of branch vessel.

FIG. 10A shows the aortic arch run showing right common carotid aneurysm. FIG. 10B shows the right subclavian run aneurysm 3.5 mm×1.6 mm, 1.5 mm neck. FIG. 10C shows the right subclavian run post hydrogel implantation showing 90% occlusion of aneurysm, all distal vessels patent. FIG. 10D shows the right subclavian run showing hydrogel within aneurysm.

DETAILED DESCRIPTION

Figure 1A:
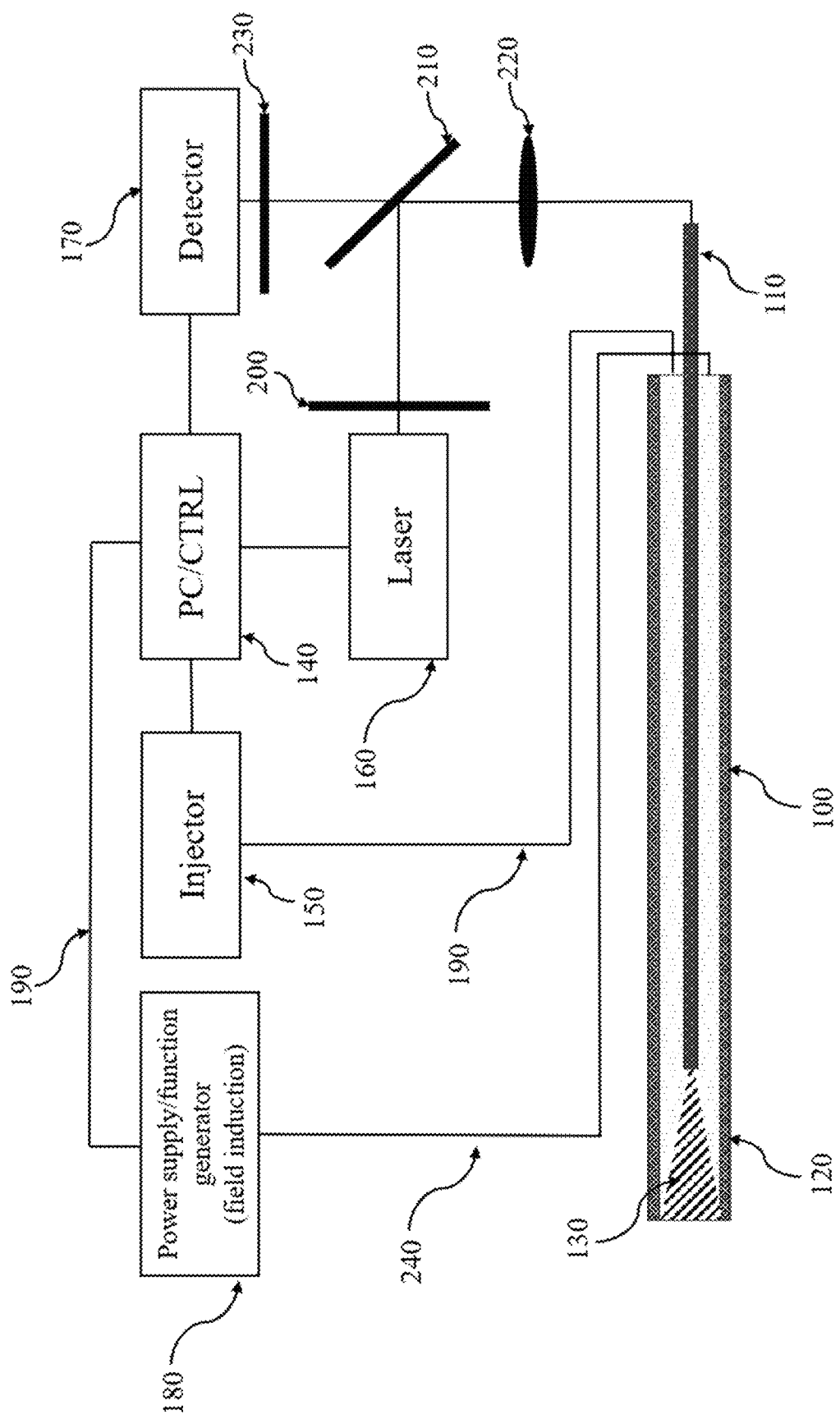
FIGS. 1A and 1B schematically illustrate a catheter system for injection and in-situ controlled crosslinking and modification of a hydrogel.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Described herein are systems, devices and associated methods that enable dynamic modification of the physicochemical properties of a hydrogel during its in vivo formation and delivery. In some example embodiments, an extended endoluminal hydrogel delivery device is employed for delivering a hydrogel (e.g. a hydrogel mass) within or a given body cavity, such as within the lumen of a blood vessels. In some example embodiments, the dynamic modification is achieved via an integrated optical fiber that modulates the degree of photo-crosslinking. In some example embodiments, this crosslinking methodology of the intravascular catheter allows for injection of low viscosity liquid hydrogel precursors which transition to a solid-state crosslinked hydrogel mass post-extrusion. Furthermore, the degree of crosslinking can be dynamically altered by changing optical intensity, allowing for extrusion of hydrogels with varying degrees of mechanical modulus to match the target, as well as modifying the diffusion rate of bioactive factors.

In some example embodiments, fully crosslinked hydrogels may be extruded in the shape of a deformable elongate member (e.g. string) and utilized in a manner or applications similar to that of metallic detachable coils. In other example embodiments, partially crosslinked hydrogels may be extruded in a semi-solid state, conforming to the shape of the target vessel or vascular network, before undergoing post-extrusion crosslinking to solidify as an embolic plug.

An example embodiment of a system for performing controlled distal crosslinking and injection is shown in FIG. 1A. In one example embodiment, the system can include a central controller (computing device, control and processing circuitry) 140, a flow device (e.g. syringe driver/injector) 150, laser 160, optical detector 170 and optical fiber/catheter assembly. The central controller140 drives the syringe pump or pump array (injector 150) to control an injection flow rate of each hydrogel precursor constituent and controls the light source 160 to dynamically vary the delivered optical power (e.g. ultraviolet (UV) optical power) to alter the chemical/physical property of the extruded hydrogels during crosslinking. The system may also be implemented to provide manual or semi-automated injection. For example, the injector 150 may optionally be decoupled from the computing device 140 for manual actuation.

The flow device 150 may be in fluid communication with a source of hydrogel precursor. Non-limiting examples of photoactivated hydrogel precursors include poly(ethylene glycol methacrylate), poly (ethylene glycol diacrylate), pluronic F-127 diacrylate, methacrylated gelatin, methacrylated hyaluronan, and methacrylated chitosan.

Some of the luminal implementations of the catheter embodiments described herein, such as the example embodiment illustrated in FIG. 1A, employ a single lumen catheter tip with an integrated optical fiber for the controlled cross-linking and injection of a hydrogel. Indeed, the example catheter shown in FIG. 1A employs a single-lumen elongate catheter sheath 100, within which a multimode optical fiber or a double-cladded fibre 110 is provided.

As shown in the figure, the distal region 120 of the catheter that extends between the optical fiber tip and the distal end of the catheter defines a reaction volume where reactions such as photo-crosslinking (triggered by the incident optical radiation (e.g. UV) emitted from the optical fiber tip as depicted by 130) and mixing take place.

In the illustrated example embodiment, the central controller 140 is operably connected to the syringe injector 150, laser 160, optical detector 170, and the power supply/function generator unit 180.

The laser 160 may comprise of an array of laser sources at varying wavelengths and powers for the purposes of photopolymerization, fluorescence excitation, and other optical detection modalities such as optical coherence tomography. Although FIG. 1A illustrates the incorporation and use of a laser 160, it will be understood that other light sources may be employed in the alternative. For example, one can employ a plurality of LEDs at multiple wavelengths, or a broadband source with a number of exchangeable filters or a liquid crystal tunable filter associated with the wavelength ranges of interest.

As described in further detail below, in some example embodiments, a field-generating means may be integrated with the distal portion of the catheter for generating one or more of an electric field, magnetic field, or ultrasound field in a distal region of the catheter where the hydrogel precursor undergoes at least partial crosslinking via the optical irradiating beam emitted by the optical fiber. This field generating means (not shown in FIG. 1A) may be controlled by a power supply and/or function generator 180 that is connected to the field generating means via connection 240 and is connected to the controller 140 via connection 190.

In one example embodiment, the controller 140 may include a user programmable feature to allow a selectable optical wavelength and/or optical power, magnetic or electric field strength, and/or hydrogel injection rate.

In some example implementations, a user may enter calibration data prior to use of the system, making it possible for the system to automatically compute the parameter values from at least one value entered. Once the injection parameter is set, the controller may employ an appropriate communication protocol (including but not limited to RS232) to send the commands to the syringe injector 150, laser 160, and/or the power supply/function generator unit 180. The syringes which are loaded onto the syringe driver are connected to the proximal end of the catheter. For example, female Luer lock ports may be provided that correspond to each lumen via a microbore tubing to minimize the additional deadspace introduced 190.

In some example implementations, the optical source (e.g. laser) may be equipped with a bandpass filter 200 to limit the range of wavelengths delivered into the optical fiber. Using a dichroic mirror 210 and a focusing lens 220, the input beam is coupled into the optical fiber.

In some example implementations, the hydrogel precursor may be loaded in a known-capacity syringe (for example, a glass 1 ml syringe for minimal injection force) and loaded onto the syringe driver.

The syringe may be connected to the catheter, for example, via connection to the injection port (the female Luer lock) of a rotating hemostatic valve (RHV) which is connected to the catheter. The optical fiber may be introduced into the catheter in a similar manner to a typical guidewire via the RHV. By aligning radiopaque markers placed at the tip of the optical fiber, the user can correctly place the optical fiber within the catheter to control the reaction volume within the catheter where the hydrogel precursor is irradiated and at least partially crosslinked.

The user may initially set the desired flow rate and the degree of crosslinking through the controller 140. In some example implementations, using pre-calibrated data, the controller can determine an initial UV delivery power to be used and begin the irradiation at a user-defined timing or triggered by presence of precursor flow at the reaction volume using optical feedback (i.e. detection of change in reflectance signal). The syringe pump will then begin to drive the syringe and the precursor is injected into the catheter.

In some example implementations, the system includes a detector that is in optical communication with a proximal end of the optical fiber, thereby facilitating the detection of optical energy that is collected from the hydrogel precursor when the hydrogel precursor is irradiated by the incident optical radiation emitted by the optical fiber. In some example implementations, the detector 170 may be a single photodetector. In other example implementations, the detector 170 may include two or more optical components. For example, the detector 170 may include multiple components including a spectrometer for the spectrally-selective detection of reflected or emitted light, and may include a balanced photodetector. The detector may include a digitizer for concurrent imaging.

In some example implementations, the detector is employed to detect optical energy reflected by the hydrogel precursor and/or optical energy that is responsively emitted by the hydrogel precursor when the hydrogel precursor is irradiated by the incident optical radiation. The reflected optical energy from the optical fiber follows a reverse path, through the dichroic mirror 210 and into the photodetector (170). The photodetector 170 is also optionally equipped with a bandpass filter (as depicted by 230) to limit the spectral range to a range of reflected signal expected. Although FIG. 1A illustrates a free-space implementation of a beamsplitter for separating the counter-propagating light within the optical fiber from the incident optical irradiation delivered by the light source, a fiber-based implementation may be employed in the alternative, for example, employing a fiber-based optical beamsplitter or optical circulator.

In addition to utilizing the optical fiber for beam delivery, it can be used in reflectance mode to monitor an optical property (and in turn physicochemical properties) of the flowing prepolymer solution (e.g. monitoring one or more spectral features or measures). An additional light source capable of delivering a suitable wavelength or wavelength range may be delivered into the optical fiber to facilitate the optical monitoring. Alternatively, a separate monitoring fiber may be provided within the catheter. For example, analysis (e.g. spectral analysis) of the reflected optical signal can be used for a multitude of purposes. One example purpose is monitoring the chemical reaction—including the crosslinking reaction of the hydrogel.

In some example embodiments, fluorescence detection may be employed to monitor the photo-crosslinking process. For example, one or more fluorophores may be added to the hydrogel precursor to facilitate fluorescence detection. In some example implementations, autofluorescence may be employed to detect or monitor the progression of photo-crosslinking of the precursor, in an alternative to, or in addition to, reflectance monitoring. Hydrogel precursor containing monomers/oligomers typically exhibit no autofluorescence. Once allowed to crosslink, however, it rapidly begins to exhibit autofluorescence as a function of aggregation and degree of crosslinking. This can in turn be used to monitor and ensure a desired level of crosslinking is achieved as the material is being deposited in vivo. An autofluorescence lookup table may be pre-determined by a calibration testing prior to the use of the device.

In some example implementations, one or more aspects of the automated system may be controlled based on a feedback measure obtained via optical detection in order to control the crosslinking of the hydrogel precursor according to control criterion. For example, a closed loop control system such as a PID controller, where the intensity or power of reflected optical energy (e.g. within a given spectral region) or fluorescence optical energy (e.g. autofluorescence value) or another optical parameter may be used as or employed to generate the feedback value. For example, deviation over/under a user-defined reference value for an optical parameter may be employed to drive the system to decrease/increase the UV power delivery to asymptotically reach a steady state. The flow rate may be controlled by the user or automatically controlled by the system.

In some example implementations, by way of incorporation of a double-cladded fiber, simultaneous delivery of wavelengths ranges typical for photopolymerization and fluorescence excitation (365~410 nm) and optical coherence tomography (1300 nm) is possible. For example, a central single-mode core of a double-clad fiber can be employed for optical coherence tomography, while the inner cladding can be employed for delivery of incident optical radiation for photo-crosslinking.

Figures 2A, 2B:
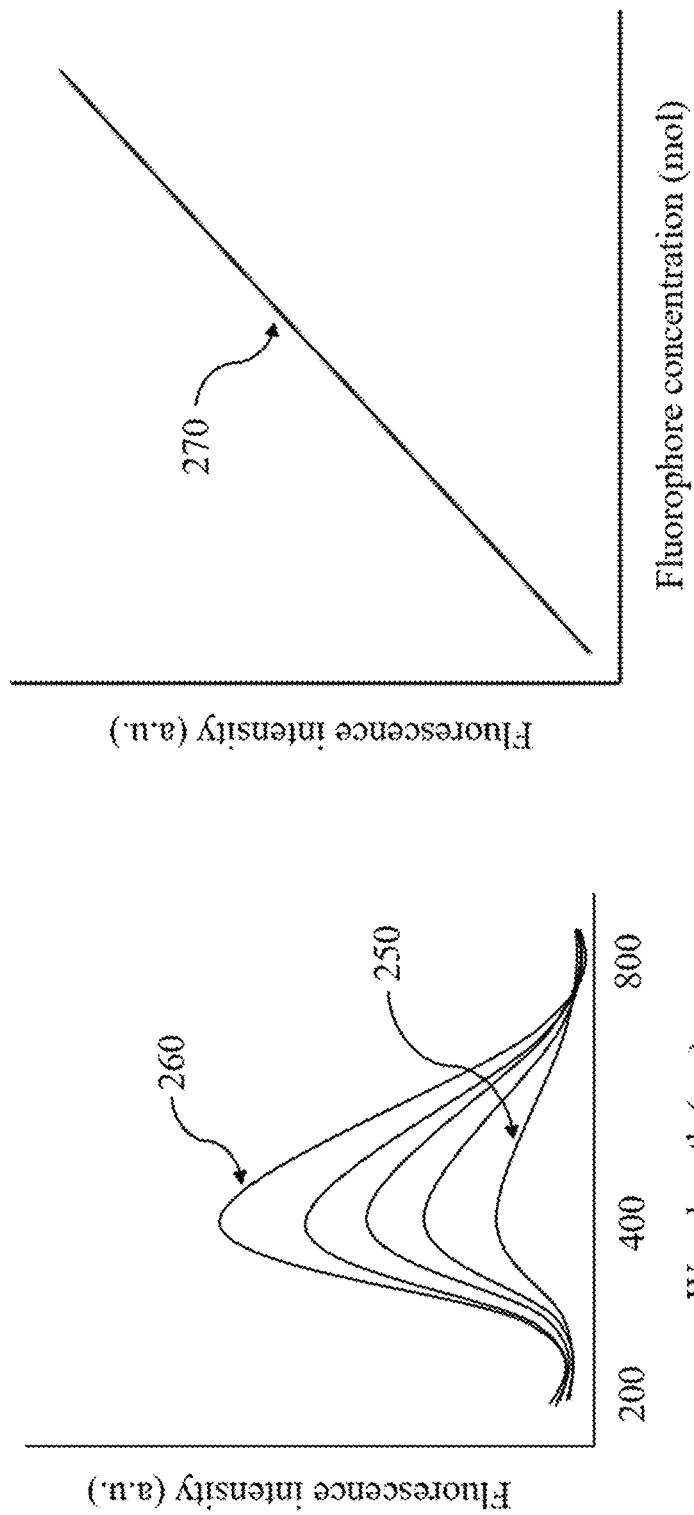
FIG. 2A plots a fluorescence spectrum from an integrated optical fiber.
FIG. 2B plots fluorescence intensity as a function of fluorophore-tagged molecular concentration in the hydrogel precursor as detected by the integrated optical fiber.

FIG. 2A plots a fluorescence spectrum obtained from the integrated optical fiber, depicting an example use case of monitoring and/or controlling the degree of crosslinking via autofluorescence measurement. Hydrogel precursors (such as synthetic and/or biologically derived photo-crosslinkable materials including poly(ethylene glycol) diacrylate), gelatin methacrylate, cellulose methacrylate, hyaluronan methacrylate, optionally with an addition of stabilizing agents such as silicate nanoplatelets), containing monomers/oligomers typically do not exhibit autofluorescence. Once allowed to crosslink, however, it rapidly begins to exhibit autofluorescence as a function of aggregation and degree of crosslinking. This can in turn be used to monitor and/or control and ensure a desired level of crosslinking is achieved as the material is being deposited in vivo. The data depicted by label 250 in FIG. 2A indicates a precursor with low degree of crosslinking (partially crosslinked semisolid) while data denoted by label 260 indicates that the precursor has formed a highly crosslinked (high modulus) hydrogel.

In some example embodiments, real-time data, such as the example data shown in

FIG. 2A, can be employed to adjust the optical power delivered in order to control the photo-crosslinking process (and thus the material properties of the formed hydrogel material). For example, one can establish an PID controller or similar feedback loop with a user-defined level of crosslinking and its corresponding autofluorescence level (which may be pre-recorded and calibrated), such that when the spectrometer receives a given level of fluorescence signal during an injection, the system may use the difference in the preset fluorescence and the current fluorescence levels to be entered into the PID controller. The controller may either change the flow rate(s) or the UV irradiance, after which the feedback may iterate over again until a desired level is reached. As often physicians may wish to fix the injection rate to suit the variety of physiological and anatomical context, if the flow rate is fixed, the system may only adjust the irradiance to achieve an appropriate level of crosslinking.

Another example use for monitoring the optical signals collected by the optical fiber is for delivering bioactive factors or drugs. For example, in an endovascular therapy, it may be desirable to deliver growth factors such as vascular endothelial growth factors (VEGF) which is commonly fluorescently tagged. The user of the proposed device may be able to ensure that a sufficient amount of VEGF was delivered to the target site by integrating the fluorescence signal over the course of the delivery period. Moreover, it is also possible to confirm the successful deposition and stabilization of the fluorescently tagged molecule by way of monitoring the fluorescence post injection while the catheter and the fibre are still at the treatment site.

Another scenario is the inject hydrogels containing moieties or added molecules that interact with the body's metabolic activity in order to produce fluorescence signal. For example, 5-aminolevulinic acid (5-ALA) is an emerging drug used clinically for margin detection as well as photodynamic therapy for glioblastomas. Briefly, 5ALA is known to preferentially get metabolized by the tumor cells to produce protoporphyrin IX which contains a fluorophore that is detected in a fluorescence guided surgery. Accordingly, in an example implementation, a 5-ALA doped hydrogel may be employed to embolize a tumor—followed by a subsequent fluorescence detection and monitoring. Other fluorescent dyes with molecular or ionic sensitivities may be employed, such as glucose, calcium, potassium, sodium, oxygen, in order to gain additional understanding of the microenvironment that the deposited hydrogel is subjected to. This may be valuable in an endovascular context, for instance, if one deposits an antiplaque drug loaded hydrogel to combat a carotid plaque and wishing to observe the dissolution/disappearance of the calcium ions via fluorescence. FIG. 2B plots fluorescence intensity as a function of fluorophore-tagged molecular concentration in the hydrogel precursor as detected by the integrated optical fiber. As depicted by data labelled 270, the concentration of fluorophore is expected to in linear proportionality with the detected fluorescence. Such fluorescence monitoring can be used during cellular or molecular delivery if the constituents have been fluorophore-tagged, to monitor the delivery process and the concentration being delivered real time.

Figure 1B:
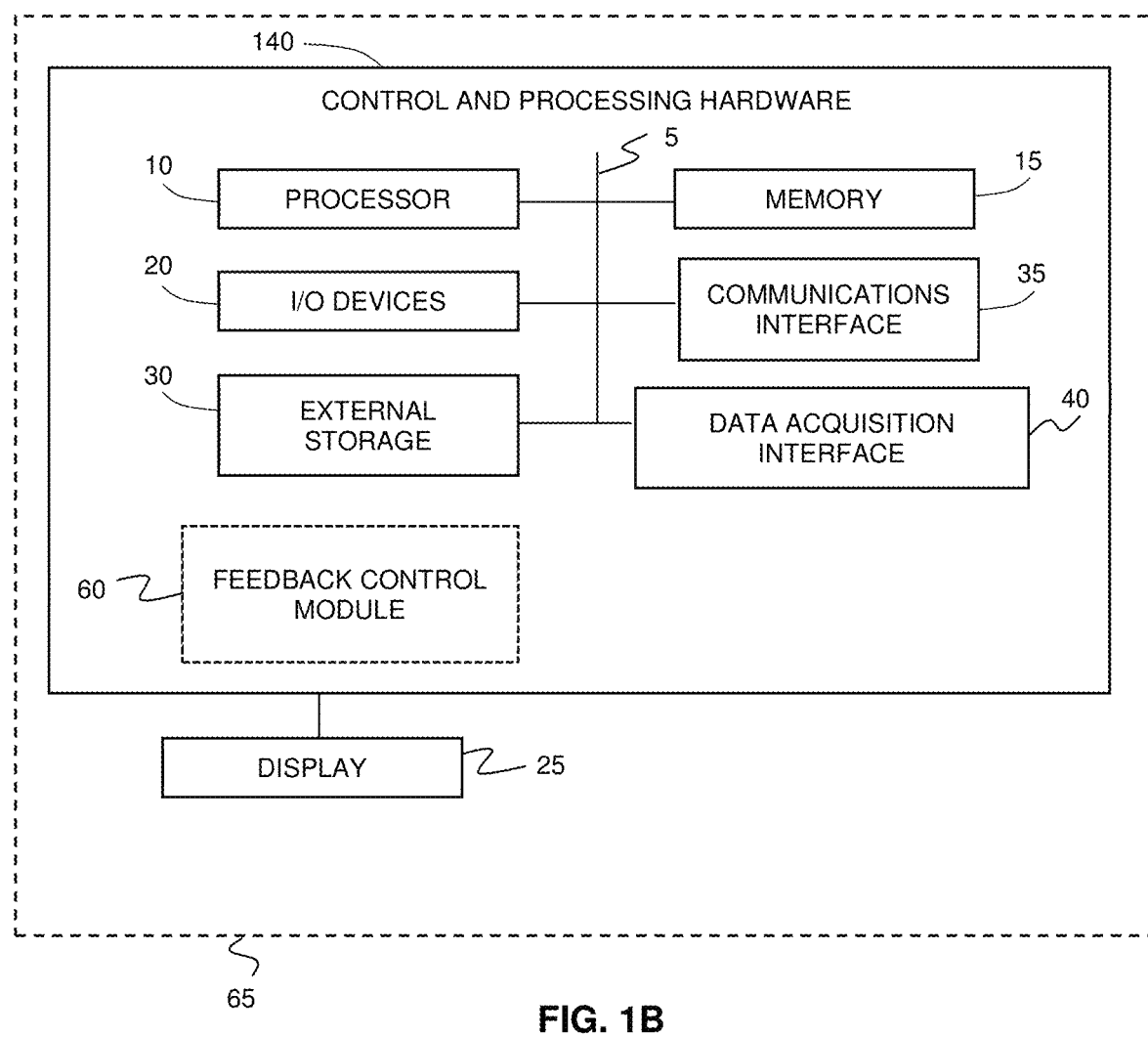

The example feedback-based control methods described herebelow can be implemented via a processor associated memory. As shown in FIG. 1B, executable instructions represented as feedback control module 60 are processed by control and processing hardware 140 to control the degree of crosslinking of a hydrogel precursor based on a feedback loop involving a signal obtained from the detector 170. The control and processing hardware 140 may include, for example, and execute instructions for performing one or more of the methods described herein, or variants thereof. Such executable instructions may be stored, for example, in the memory 15 and/or other internal storage. Additional control modules may be provided. As shown in FIG. 1A, the example control and processing hardware may include, for example, one or more input/output devices 20, a display 25, external storage 30, a communications interface 35, and a data acquisition interface 40. The display 25 may be integrated with the control and processing hardware 140, as shown by the dashed line 65.

The methods described herein can be partially implemented via hardware logic in processor 10 and partially using the instructions stored in memory 15. Some embodiments may be implemented using processor 10 without additional instructions stored in memory 15. Some embodiments are implemented using the instructions stored in memory 15 for execution by one or more microprocessors. Thus, the disclosure is not limited to a specific configuration of hardware and/or software.

It is to be understood that the example system shown in the figure is not intended to be limited to the components that may be employed in a given implementation. For example, the system may include one or more additional processors. Furthermore, one or more components of control and processing hardware 140 may be provided as an external component that is interfaced to a processing device. Furthermore, although the bus 5 is depicted as a single connection between all of the components, it will be appreciated that the bus 5 may represent one or more circuits, devices or communication channels which link two or more of the components. For example, the bus 5 may include a motherboard. The control and processing hardware 140 may include many more or less components than those shown.

Some aspects of the present disclosure can be embodied, at least in part, in software, which, when executed on a computing system, transforms an otherwise generic computing system into a specialty-purpose computing system that is capable of performing the methods disclosed herein, or variations thereof. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine-readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

Figure 3C:
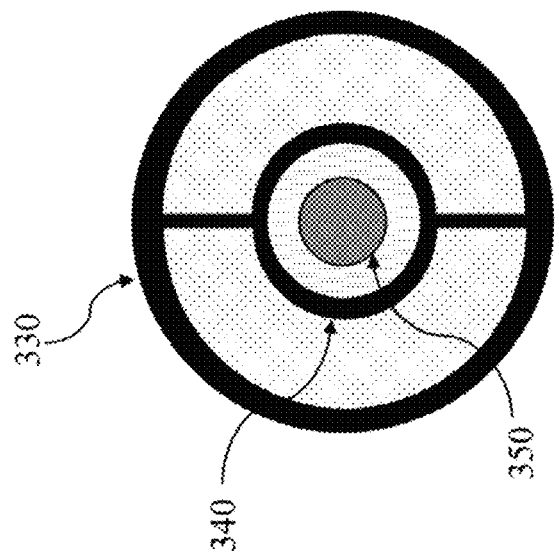
FIG. 3C illustrates a luminal cross-sectional view of an example optical fiber integrated catheter having a triple lumen featuring double-D lumens for fluid delivery and a dedicated optical fiber channel in the center
Figure 3B:
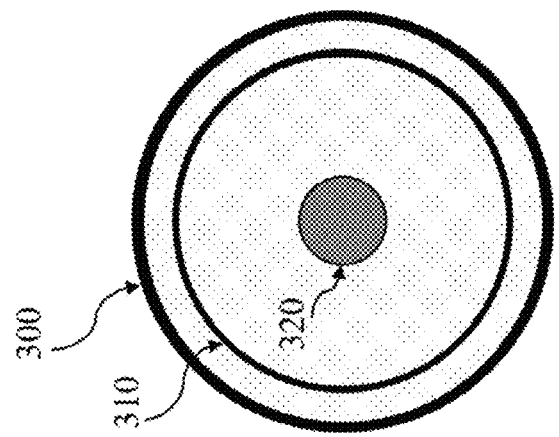
FIG. 3B illustrates a luminal cross-sectional view of an example optical fiber integrated catheter having a dual lumen, where the two lumens are coaxial and the optical fiber is housed within the inner lumen.
Figure 3A:
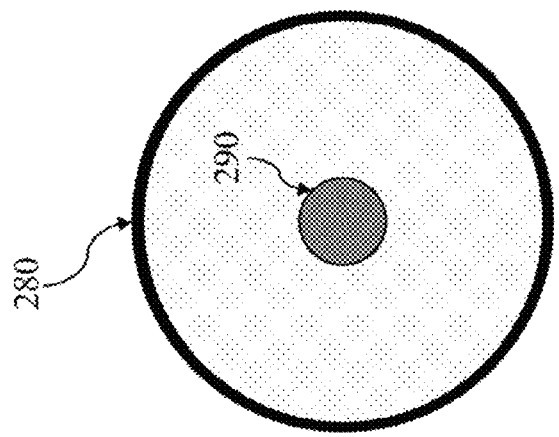
FIG. 3A illustrates a luminal cross-sectional view of an example optical fiber integrated catheter having a single lumen with a coaxially-positioned optical fiber.

Referring now to FIGS. 3A-3D, a number of example embodiments are illustrated that show single (FIG. 3A) and multilumen (FIGS. 3B-3D) catheters for the controlled crosslinking, property control, and injection. FIG. 3A illustrates a catheter that includes a single sheath 280 which houses, within a single lumen, a beam-delivering optical fiber labelled 290, which may or may not be removable but in either case allows precursors and/or other fluids to travel around the fiber within the intraluminal space.

Figure 3D:
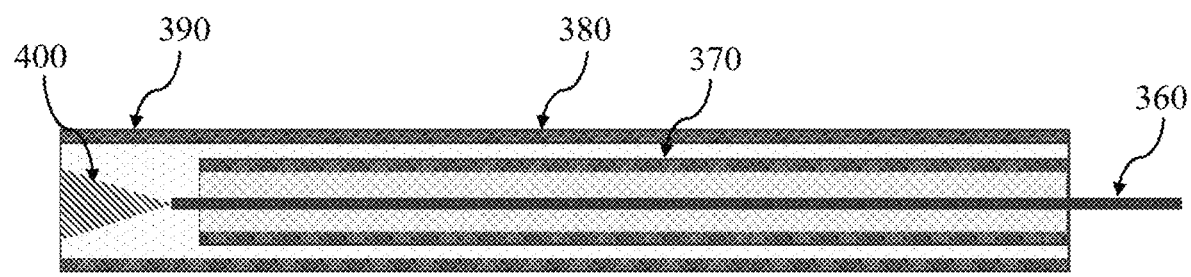
FIG. 3D illustrates a side view of an example catheter in which the optical fiber tip is recessed within the catheter tip. The figure illustrates an example multilumen embodiment where multiple lumens merge into a single lumen prior to a distal single-lumen region of the catheter that extends to the distal end (tip) of the catheter. The distal single-lumen region of the catheter that extends between the proximal multilumen region and the end of the catheter referred as a reaction chamber.

FIGS. 3B and 3D illustrate an example coaxial double lumen configuration where the outer sheath labelled 300 can be used to introduce another injectable material, such as, but not limited to, another photo-crosslinkable hydrogel precursor. The inner conduit labelled 310, which encloses an inner lumen, as well as the optical fiber housed within, labeled 320 for example, such a secondary hydrogel precursor can be provided to form a 'jacket layer'. For example, the inner lumen of the inner conduit 310 may shield a drug-carrying precursor in the inner lumen flow, or to carry a different type of drug and/or cells (non-limiting examples include doxorubicin, polyglycolic acid, polylactide, vascular endothelial growth factors (VEGF), fibroblast growth factors (FGF), and endothelial progenitor cells) to deliver multiple constituents that are differentially released over time (outer layer releases faster than inner layer).

In one example implementation, the outer lumen (defined between the outer sheath 300 and the inner conduit 310) can be used to provide a sheath flow. In some example embodiments, the sheath flow may not be crosslinkable. Such an inert material undergoes laminar flow and does not mix with the inner lumen flow within the single-lumen reaction volume, and can, for instance, be used to hydrodynamically focus the inner lumen flow or to help reduce the wall shear that the inner lumen flow would otherwise be subjected to.

FIG. 3D illustrates a side view of an example catheter in which the optical fiber 360 is recessed within the distal region of the catheter. The figure illustrates an example multilumen embodiment where multiple lumens (namely an inner lumen enclosed within the inner conduit 370 and an outer lumen defined between the inner conduit 370 and the outer sheath 380) merge into a single lumen within a distal single-lumen region 390 of the catheter, prior to emerging from the distal end of the catheter, where the distal single-lumen region extends to the distal end (tip) of the catheter. The distal single-lumen region of the catheter that extends between distal end of the inner conduit 370 and the distal end of the outer sheath 380 of the catheter may function as a reaction chamber 390 within which incident optical radiation 400 emitted from the distal end of the optical fiber at least partially photo-crosslinks extruded hydrogel precursor within the catheter prior to its ejection into a bodily lumen or region.

In the double-lumen example embodiment illustrated in FIG. 3B, the inner lumen 310 may be established by a second conduit that is inserted within the outer lumen 300 of the catheter, as noted above. In another example embodiment, the catheter may employ an outer sheath that includes both a primary lumen for housing the optical fiber and a secondary lumen for injecting the additional material.

FIG. 3C illustrates an example triple-lumen structure having a double-D shape fluid delivery lumens housed within an outer sheath 330 along with a dedicated central lumen housed within an inner conduit 340, where the optical fiber 350 resides within the inner lumen. This type of multiluminal architecture can be extruded as a monolithic (single piece) structure, and a distal single-lumen region defining the reaction chamber can be later added to the tip to complete the catheter. Each lumen may be in fluid communication with a respective separate injection port such that multiple syringes loaded with different constituents may be separately injected. Saline can be flushed in the inner lumen to maintain the optical fiber afloat and centred within the lumen. The central lumen for the optical fiber facilitates changes in the position of the fiber, which may be employed, for example, to control changes to the crosslinking process, as discussed elsewhere.

Figure 3E:
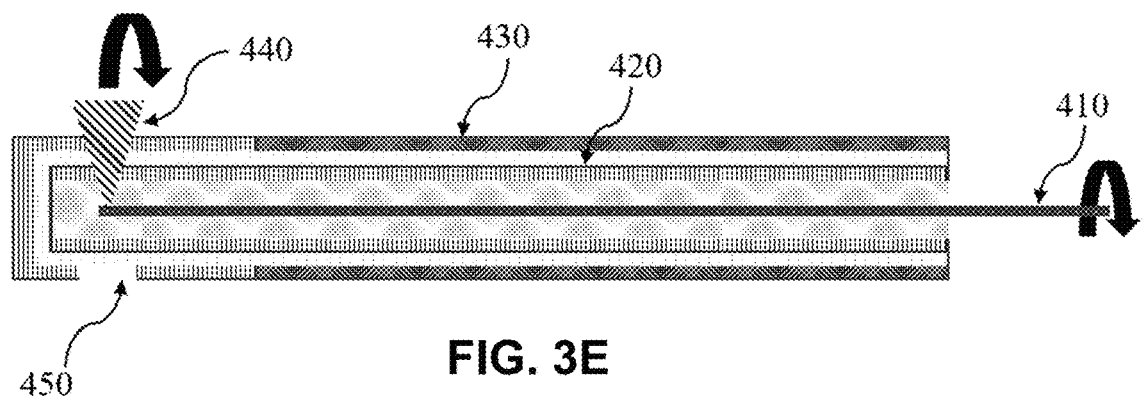
FIG. 3E illustrates a side view of an example catheter including an optical fiber configured to direct the photo-crosslinking beam in a side direction during rotation of the fiber.

FIG. 3E illustrates another side view of an example catheter in which the optical fiber 410 is rotating, for example by way of using a fiber optic rotary joint (FORJ) residing at a proximal end of the catheter. The optical fiber resides within a photopermeable inner conduit labelled 420. Outer sheath 430 is partially made transparent at the distal end to allow the delivered beam 440 to radially exit the catheter and reflected back from the tissue. In some example implementations, hydrogel precursor may be flowed through the outer lumen between the outer sheath 430 and the inner conduit 420, and a non-crosslinkable liquid such as saline may be flowed through the inner lumen. In this configuration a side-firing optical fibre (e.g. as illustrated in FIG. 4D) is used to perform one or more of photopolymerization, fluorescence detection, and optical coherence tomography imaging. For instance, a dual autofluorescence-optical coherence tomography guided injection of a hydrogel is possible by aligning the imaging plane (radial from the fiber tip) and the injection port 450 near the tip of the catheter on the side.

The preceding multilumen catheter embodiments may provide the ability to combine the optical control the polymer matrix properties of the extruding hydrogels with secondary and/or tertiary modification methods. For example, one or more additional lumens may be employed to facilitate secondary crosslinking of an orthogonal network via another crosslinking method such as ionic crosslinking. Ionically crosslinked precursors include but are not limited to alginate, chitosan, kappa-carrageenan, and gellan gum. For example, a coaxial dual lumen architecture may be employed to introduce a sheath flow an ionic crosslinker from the outer lumen while the precursor including ionically crosslinkable network flows within the inner lumen. In some example embodiments such as FIG. 3B or similar, an inert fluid (such as water or glycerol) can be introduced via the outer lumen and the diameter of the extruded hydrogel (via inner sheath) can be adjusted by modulating the relative flow rates of the prepolymer solution and the supporting material. Generally, the diameter of the extruded hydrogel can be decreased by increasing the outer/inner flow rate ratio and vice versa.

In some example implementations, coaxial hydrogel string structures can be extruded by flowing two types of precursors in the inner and outer lumens of a double-lumen catheter simultaneously. In a similar manner to the diameter modulation of extruded hydrogel via sheath flow rate, by modulating the outer and inner precursor flow, the polymerized hydrogel may be tuned to have various core/shell ratios. The core/shell ratio of the extruded coaxial hydrogel is a function of the inner/outer flow rate.

In some example embodiments, different constituent can be sequentially injected to produce a continuous hydrogel extrusion with alternating properties length wise.

Figure 4A:
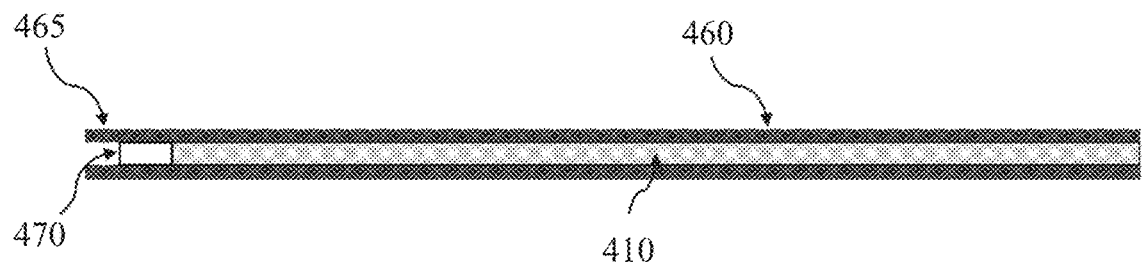
FIG. 4A illustrates an example optical fiber configuration in which the entire length of the fiber is coated with a hydrophobic housing layer to reduce adhesion to the prepolymer solution and therefore increased internal pressure, and where a gradient-indexed (GRIN) lens is added to prevent the light loss due to the scattering against the housing layer by projecting the focal point to a finite distance away from the fiber tip.
Figure 4B:
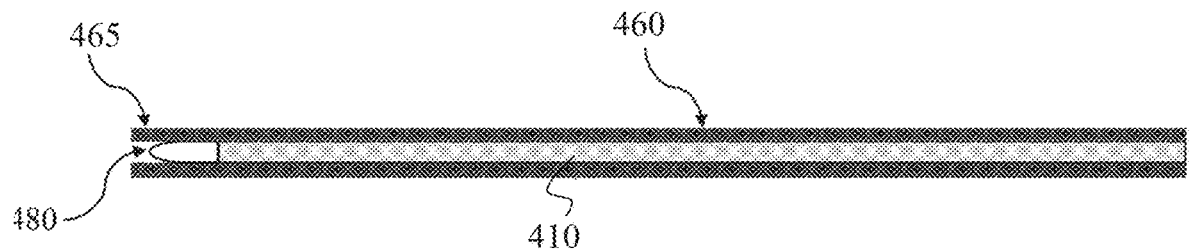
FIG. 4B illustrates an example optical fiber configuration in which the entire length of the fiber is coated with a hydrophobic housing layer to reduce adhesion to the prepolymer solution and therefore increased internal pressure, and where a ball lens is added to prevent the light loss due to the scattering against the housing layer by projecting the focal point to a finite distance away from the fiber tip.
Figure 4C:
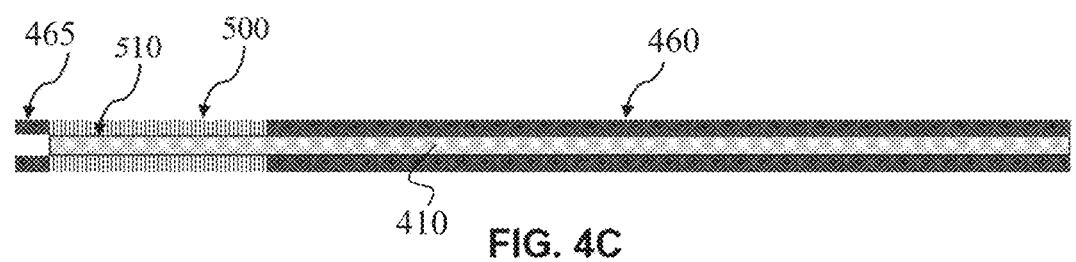
FIG. 4C illustrates an example optical fiber design that includes a diffuse tip fiber where light is radially distributed across a finite length of the fiber tip. Aligned with this diffuse section of the optical fiber is a photopermeable jacketing layer to allow the light to reach the flowing prepolymer solution while also preventing unwanted adhesion by way of hydrophobicity.
Figure 4D:
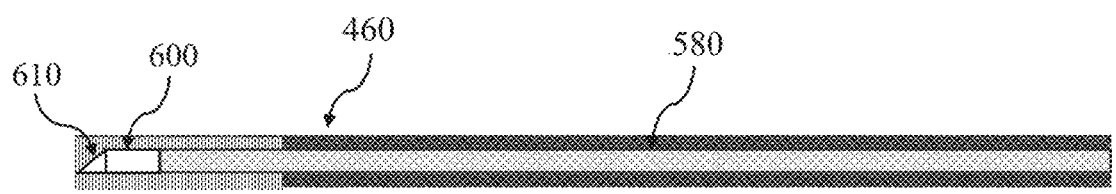
FIG. 4D illustrates an example embodiment involving a side-firing optical fiber configuration suitable, for example, for concurrent optical coherence tomography imaging and photo-crosslinking.

FIGS. 4A-4D illustrate example embodiments involving the incorporation of an optical fiber within the catheter (FIGS. 4A-4C only show the optical fiber and associated components, but do not show the catheter walls that define the one or more lumens described above). At least a portion of the entire length of the fiber may be coated or otherwise contacted with a hydrophobic layer 460 to reduce adhesion to the prepolymer solution and therefore increased internal pressure. Optical fiber 410 is nominally multimode to accommodate generally efficient beam delivery and detection of fluorescence signals, but are not limited. For instance, multiple cladding can be used to accommodate multiple wavelengths.

As shown in the figures, a lens (e.g. a gradient indexed (GRIN) lens 470 shown in FIG. 4A or a curved lens 480 shown in FIG. 4B can be added to prevent the light loss due to the scattering against the hydrophobic layer by projecting the focal point to a finite distance away from the fiber tip.

To prevent the flowing hydrogel precursor fluid from coming into direct contact with the fiber tip (which in turn may cause the precursor to adhere and clog the catheter lumen), the optical fiber tip (and optionally the associated distal focusing elements) may be recessed into a distal housing/jacket layer, as shown in label 465.

FIG. 4C illustrates an example embodiment in which a diffuse tip fiber is employed, where light emitted by the optical fiber is distributed (peripherally, e.g. in the radial direction) across a finite length 510 (a distal optical diffusing region) of the optical fiber. As shown in the figure, a photopermeable jacketing layer 500 may be aligned with this diffuse section (which will have its cladding removed, then a photopermeable jacketing is applied) of the optical fiber to allow the light to reach the flowing prepolymer solution while also preventing unwanted adhesion by way of a combination of hydrophobicity and hydrophilicity.

FIG. 4D represents a side-firing configuration suitable for concurrent optical coherence tomography imaging, comprising of double cladded fiber 580, GRIN lens 600, and either a mirror, prism or a no-core fiber cleaved at 45 degree angle (610) to direct the light radially. This type of fiber can be used in the catheter configuration seen in FIG. 3E to perform concurrent photopolymerization and imaging.

Figure 5:
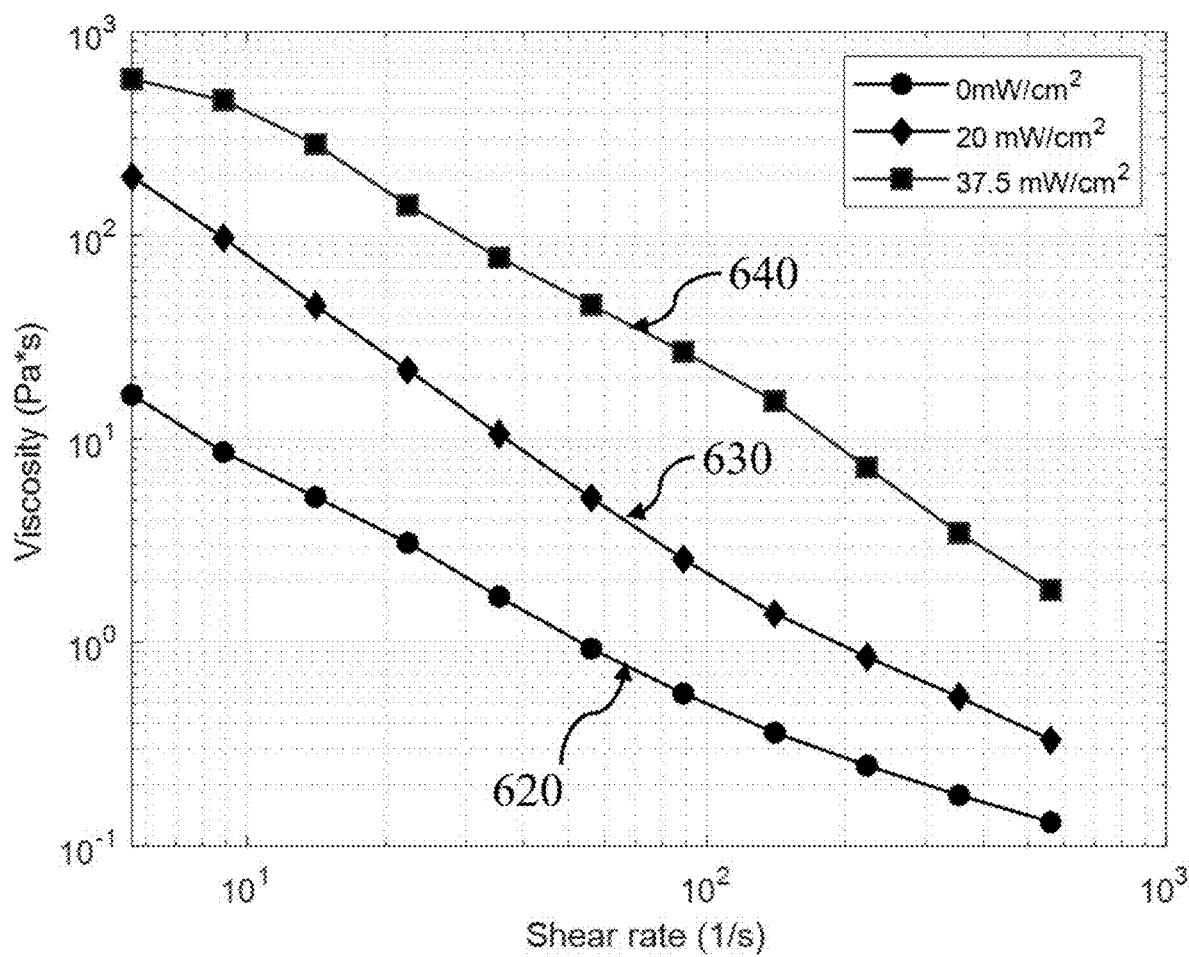
FIG. 5 plots that dependence of viscosity of a poly (ethylene glycol) diacrylate) based hydrogel precursor on shear rate when extruded using an example hydrogel injection catheter. The irradiation power was tested at 0, 20, and 37.5 mW and demonstrates the mechanical tunability of the hydrogel extruded from this device.

FIG. 5 plots the dependence of viscosity on shear rate for a poly(ethylene glycol diacrylate) based hydrogel precursor (15 wt % PEGDA, 4 wt % Laponite XLG nanosilicate platelet, dissolved in deionized water) for different optical power values of optical irradiation at a wavelength of 405 nm. This testing was done with a single lumen microcatheter (0.8 mm diameter), housing a 200-micron multimodal optical fiber coated by Hytrel™ thermoplastic with flat-cleave tip, which is recessed into the Hytrel layer by 1 mm. The reaction volume residing between the optical fiber tip and the catheter tip, was 5 mm. The flow rate used here was fixed at 0.2 ml/min. As shown in the figure, proposed system has the ability to tune the hydrogel's physical parameter as a function of optical power delivered. At a fixed precursor flow rate, the viscosity of the ejected hydrogel precursor without irradiation shows the lowest shear rate dependent viscosity across the entire range. With increased UV irradiation (20 and 37.5 mW/cm$^2$), the increased degree of crosslinking leads to a higher viscosity—with an operable dynamic range being from $10^{-1}$ Pa·s to $10^3$ Pa·s. The irradiation intensity was tested at 0(labeled 620), 20 (labeled 630), and 37.5 (labeled 640) mW/cm$^2$ and demonstrates the mechanical tunability of the hydrogel extruded from this device. This preliminary result shows that is it possible to optically modulate the physicochemical properties of a given hydrogel formulation in concert with the injection process. The ability to modulate the extruded viscosity (and therefore mechanical stability) is favourable in endovascular injections where depending on the vessel size, morphology and the nature of the local hemodynamics, the optimal mechanical property of injectable hydrogels may change. Though in this particular experiment was carried out to quantify the viscosity of the hydrogel precursor, the principle can apply to any parameter that can be photomodulated, such as tunable delivery of photoactivated drugs.

Figure 6:
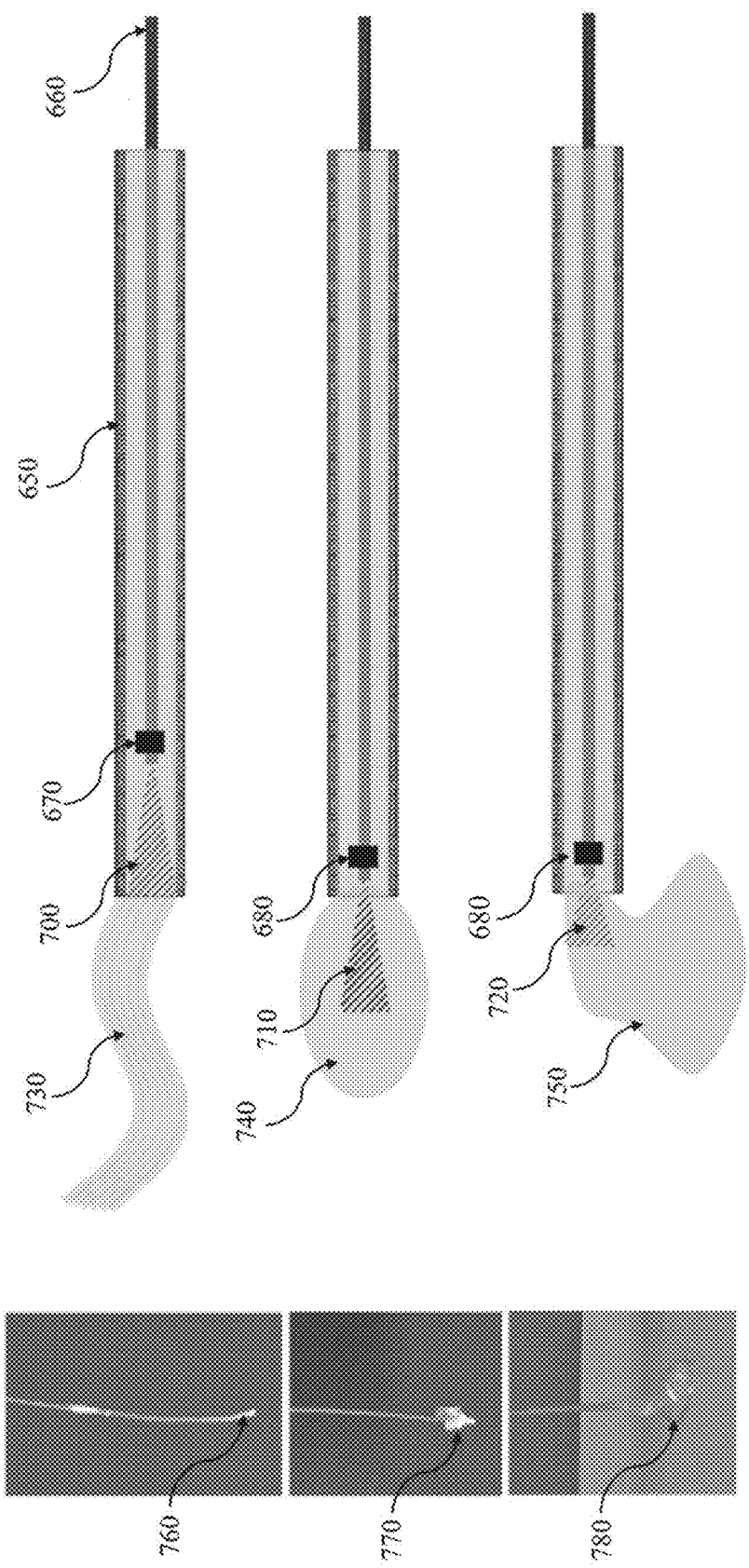
FIG. 6 provides a schematic representations and corresponding photographs for various hydrogel extrusion modes. High intensity UV irradiation (~50 mW) results in a fully crosslinked string of hydrogel to be extruded (top). While maintaining the high irradiance, it is possible to yield a spheroid shaped hydrogel by advancing the optical fiber closer to the catheter tip (middle). By reducing the optical irradiance, a partially crosslinked semisolid of varying viscosities can be extruded (bottom).

In some example embodiments, the length of the reaction volume (i.e. the region between the fiber tip and the catheter lumen tip), can be altered to extrude a number of different hydrogel geometries. For example, as shown in FIG. 6, placing the optical fiber tip (forward firing) proximal (as seen by the position of the radiopaque marker 670 with respect to the position of the catheter outer sheath 650) relative to the distal end of the catheter results in the polymerization reaction taking place throughout an extended reaction volume, resulting in a string shape hydrogel (schematically shown 730, photograph shown as 760) to be extruded. To form a spheroid (schematically shown 740, photography shown as 770), the optical fiber can be advanced to the distal end (labeled 680) of the catheter. As illustrated in FIG. 6 label 700, high intensity UV irradiation (~50 mW/cm$^2$) results in a fully crosslinked string of hydrogel to be extruded (top). While maintaining the high irradiance, it is possible to yield a spheroid shaped hydrogel by advancing the optical fiber closer to the catheter tip (label 710). By reducing the optical irradiance (720), a partially crosslinked semisolid (schematically shown 750, photograph shown as 780) of varying viscosities can be extruded (bottom).

Figure 7A:
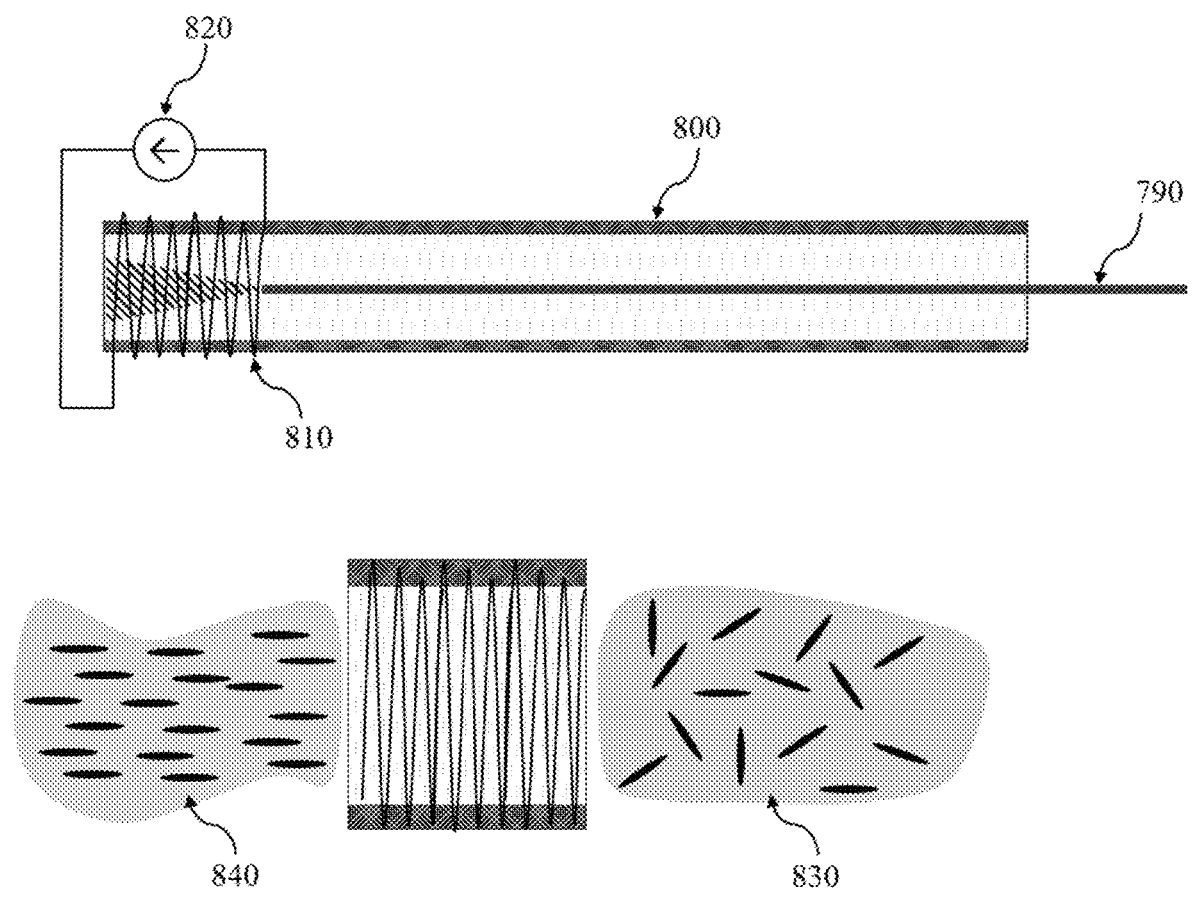
FIGS. 7A, 7B and 7C provide schematic views of magnetic, electric, and acoustic field hydrogel modification mechanisms of the catheter device, respectively.
Figure 7B:
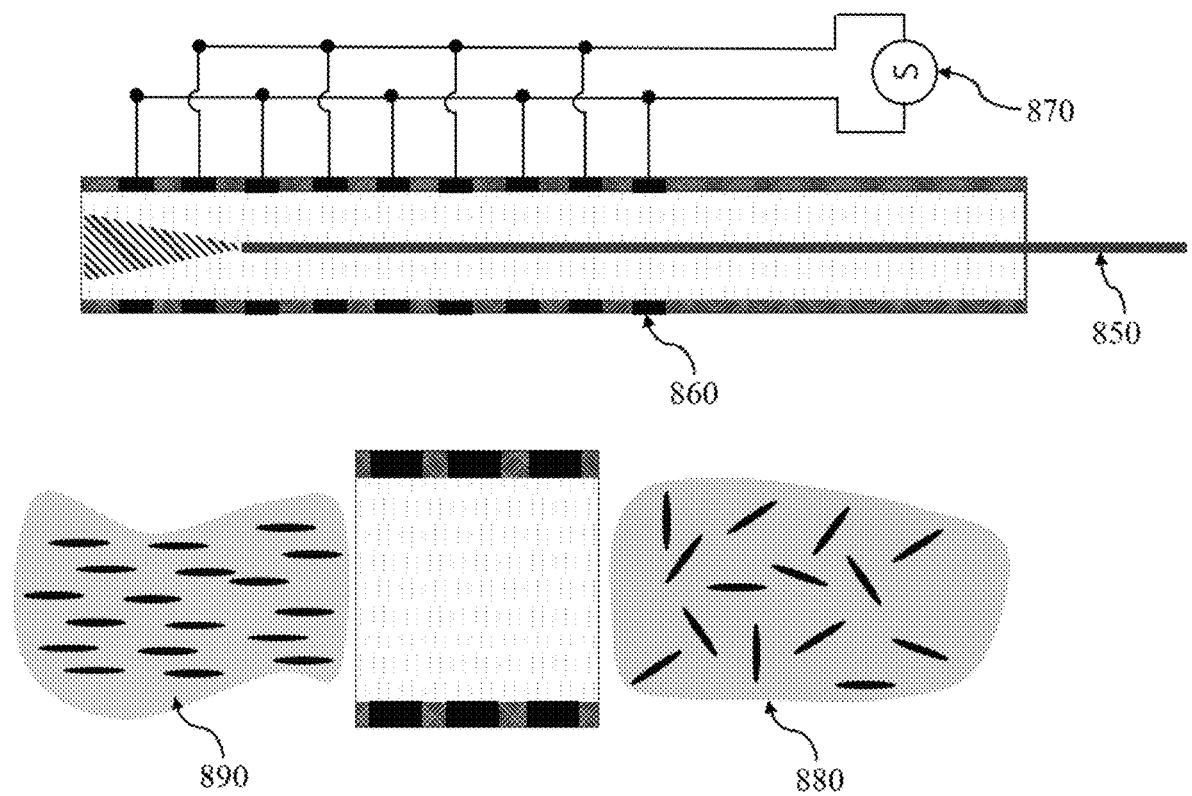

Using an alternative set of embodiments shown in FIGS. 7A and 7B, further modifications to the hydrogel matrix can be made through the application of electromagnetic fields. This can be employed in conjunction with the optical modification method or as a standalone method.

More specifically, in the embodiment shown in FIG. 7A, one can apply a magnetic field in a direction parallel to the axis of the catheter body by applying electrical current across the coil (810) embedded in the distal end of the catheter 800. The field strength can be adjusted by the magnitude of the electrical current (820). The applied magnetic field can be used to spatially align magnetically active constituents/dopants (as seen schematically in 830 and 840), such as magnetic nanoparticles (MNPs) and magnetic nanorods within the hydrogel in conjunction with injection and crosslinking (by way of photo-crosslinking using optical fiber based beam delivery discussed above, labeled 790) to form a magnetically tem plated hydrogel network with anisotropic morphology. When the precursor containing magnetically active constituents such as magnetic nanoparticles, they tend to align with the field, resulting in an extruded hydrogel containing anisotropic properties. Power is applied to the coil via external supply—electrical connection established via the catheter body—similar to ablation catheters. The applied magnetic field can also be used to magnetothermally modulate the local precursor temperature for various purposes including but not limited to inducing thermally initiated reactions and activating drug release.

In the example electric field hydrogel modification mechanism shown in FIG. 7B, a series of electrodes (860) integrated at the distal end of the catheter is powered to induce an AC electric field (870) that is in in a parallel direction to the precursor flow within the catheter body while the patterned morphology can be 'locked' by way of photo-crosslinking via fiber delivered beam (850). Power is applied to the electrode array via electrical connection, established via the catheter, with an external supply. For example, one can apply an electric field in a direction parallel to the axis of the catheter body by applying AC radiofrequency electrical voltage across an alternating array of ring shaped electrodes embedded in the distal end of the catheter. The electric field strength can be adjusted by the magnitude of the electrical voltage. When the precursor containing electrically conductive constituents such as carbon nanotubes, they tend to align with the field, resulting in an extruded hydrogel containing anisotropic properties. The applied electric field can thus be used to spatially align electrically conductive constituents/dopants (as seen schematically in 880 and 890), such as carbon nanotubes (CNTs), graphene, and silver nanowires within the hydrogel in conjunction with injection and crosslinking to form an electric field templated hydrogel network with anisotropic morphology. Such electrically aligned conductive constituents may increase the overall conductivity of the extruded hydrogel, such that when used in cardiac/nervous tissue applications the improved conductivity may be beneficial. Anisotropic morphology within an extruded hydrogel may yield non-exclusive properties such as anisotropic mechanical strength, electrical conductivity, ionic conductivity/molecular permeability to suit particular application.

Figure 7C:
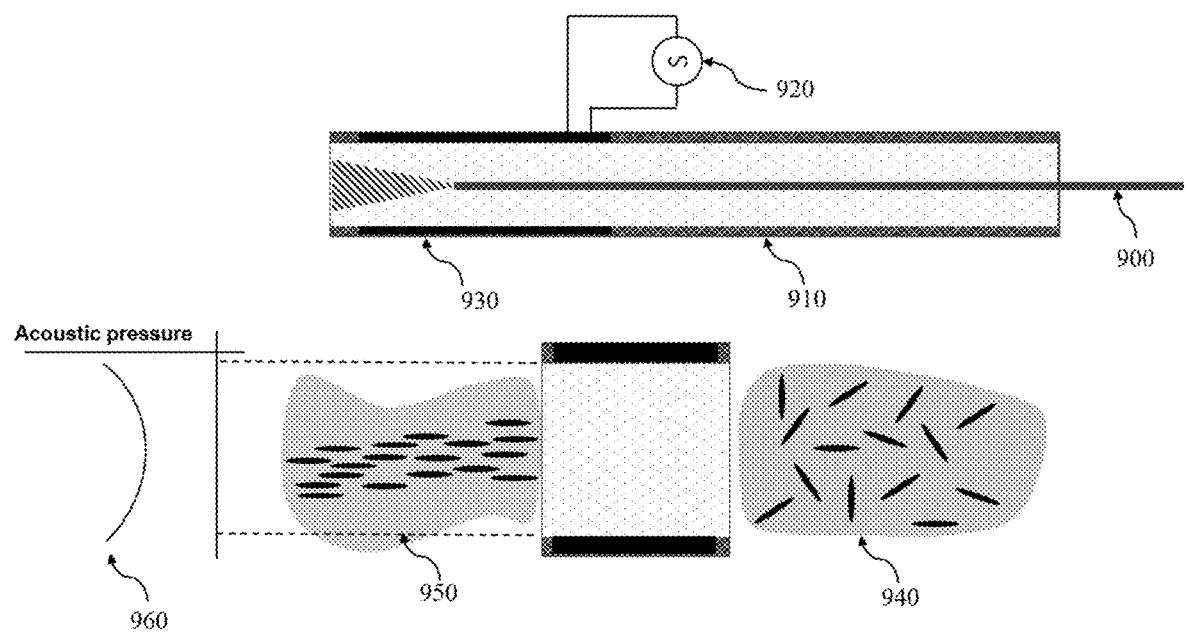

Moreover, in an alternative embodiment shown in FIG. 7C, it is possible to acoustically induce longitudinal alignment by way of creating a node at the centre of the cross-section of the catheter lumen. The transducer (930), made of traditional piezoelectric material such as PZT or flexible PVDF, can be shaped in a rectangular or ring shape and can be placed (affixed to the catheter, such as via an adhesive) in an orientation such that their actuation is orthogonal to the longitudinal axis of catheter lumen and be driven by an external AC supply (920). For instance, by placing a ring transducer which 'cuffs' over the catheter lumen (with the catheter sheath being shown at 910), producing radial actuation at a resonant frequency of 500 kHz, this will create an acoustic field with a wavelength of approximately 3 mm (with speed of sounds in water assumed to be approximately 1480 m/s). If the diameter of the catheter lumen is 1.5 mm, then the acoustic pressure will have its node at 0.75 mm, or the centre of the lumen (as shown schematically in 960), allowing additives such as nanoparticles, macromolecular drugs, cells, and the like to migrate towards the centre of the lumen (as schematically shown in 940 and 950) while being injected across this segment of the catheter. Similarly to the other two alignment mechanisms, this acoustically aligned flow of precursor can then be photo-crosslinked via a fiber delivered (900) beam at the distal end of the catheter.

The coil or array electrodes or acoustic transducers referred to above and illustrated in FIGS. 7A, 7B, and 7C may be provided as system components that are operably coupled to the controller unit. For example, referring again to FIG. 1, the power supply/function generator unit (180), which is also driven by the controller unit 140, may be used to power the coil or the electrode array embedded at the distal segment of the catheter (as depicted by the connection labelled 150). The controller unit may be employed to adjust the magnitude of current/voltage as well as the frequency depending on the desired hydrogel properties.

As described above, the opto-magnetic as well as opto-electrical modification of the flowing hydrogel precursor can be performed in concert. For example, an opto-magnetic modification mechanism can work by magnetically aligning the active ingredients more proximal to the location of the optical irradiation, such that the alignment is subsequently locked by the photo-crosslinking. Similarly, electric field can be used to align field-polarizable materials.

EXAMPLES

The following examples are presented to enable those skilled in the art to understand and to practice embodiments of the present disclosure. They should not be considered as a limitation on the scope of the disclosure, but merely as being illustrative and representative thereof.

The tunability of hydrogel described above has been tested preliminarily in animal models including porcine renal vessels (vascular tumor analogue), porcine subclavian and femoral arteries (high flow, major vessel), porcine rete mirabile (arterial to arterial network), and rabbit elastase aneurysm model. For the renal vessels, we observed that lower UV irradiance and correspondingly injection of lower modulus hydrogel mass into the renal capillary network resulted in a suitable embolization. Maximum UV irradiance was employed to ensure a fully crosslinked hydrogel mass was extruded when embolizing the subclavian or the femoral arteries to provide a sufficient blocking force to the high flow. Finally in the rete mirabile, a medium irradiation was chosen such that the there is a sufficient penetration by the injected material into the capillary network while preventing leakage into the contralateral artery.

Figure 8A:
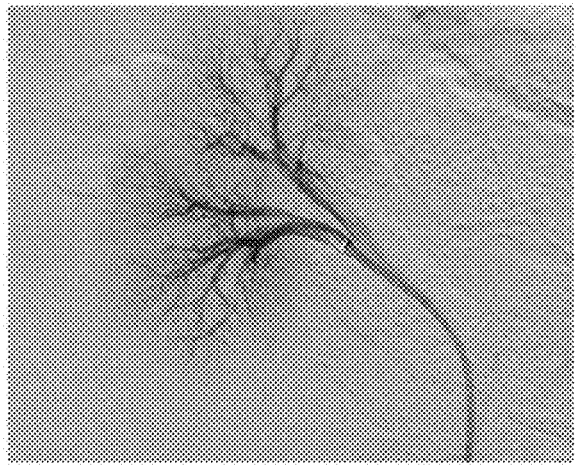
FIGS. 8A, 8B, 8C and 8D demonstrate swine embolization of capillary networks according to the methods described herein.
Figure 8B:
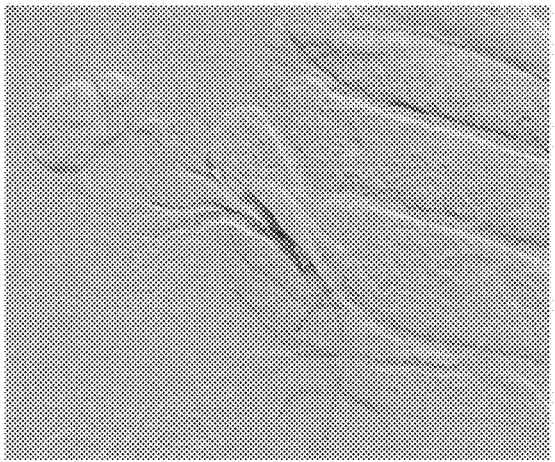

As a preliminary demonstration in preclinical settings, the system was simplified to accommodate the operator's hand injection, while the laser power could be modulated as needed. Successful occlusion by poly(ethylene glycol diacrylate) based hydrogel injection using the proposed delivery system is shown in FIGS. 8A-8D. FIGS. 8A and 8B show pre- and post-renal embolization (full casting of renal tree), respectively. In this case, a Pneumbra 3Max catheter 4.7 F (1.27 mm distal outer diameter) housing a 200-micron multimodal optical fiber emitting <10 mW/cm$^2$ at 365 nm was used to deliver 3 ml of the hydrogel formulation (15 wt % PEGDA, 8 wt % Laponite XLG nanosilicate platelet, dissolved in 50/50 vol % Omnipaque 300 contrast/DI water).

Figure 8C:
Figure 8D:
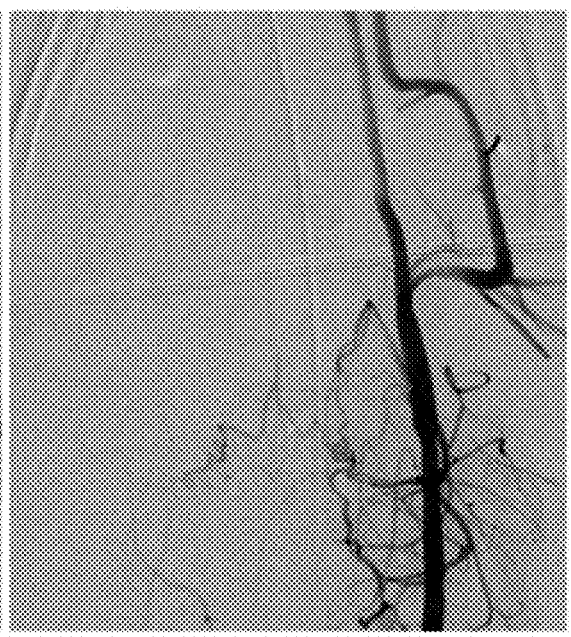

FIG. 8C shows pre-hydrogel-injection common carotid artery injection showing filling of ascending pharyngeal artery (APA) into rete mirabile and filling of external carotid artery (ECA) vessels towards the face/jaw. FIG. 8D shows post-hydrogel-injection common carotid artery showing embolization of rete mirabile, APA, and ECA branches. No filling of contralateral rete and APA is observed. In this case, an Excelsior® XT27 catheter 2.7 F (0.914 mm distal outer diameter) housing a 200-micron multimodal optical fiber emitting <10 mW/cm$^2$ at 365 nm was used to deliver 3 ml of the hydrogel formulation (15 wt % PEGDA, 8 wt % Laponite XLG nanosilicate platelet, dissolved in 62.5/37.5 vol % Omnipaque 300 contrast/DI water).

Figure 9A:
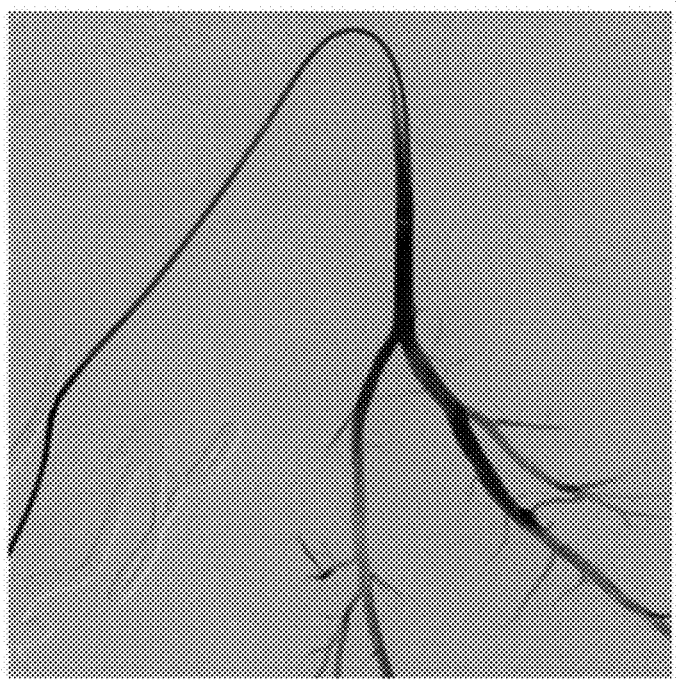
FIGS. 9A, 9B, 9C and 9D demonstrate swine embolization experiment of various arteries according to the methods described herein.
Figure 9B:
Figure 9C:
Figure 9D:

FIGS. 9A-9D demonstrate swine embolization experiment of various arteries according to the methods described herein. FIG. 9A shows pre embolization of common femoral artery tree, while FIG. 9B shows 5 min following embolization (6 cc injected); internal iliac now occluded. In this case, a Pneumbra 3Max catheter 4.7 F (1.27 mm distal outer diameter) housing a 200-micron multimodal optical fiber emitting <10 mW/cm$^2$ at 365 nm was used to deliver 3 ml of the hydrogel formulation (15 wt % PEGDA, 10 wt % Laponite XLG nanosilicate platelet, dissolved in 62.5/37.5 vol % Omnipaque 300 contrast/DI water). FIGS. 9C and 9D show pre and post injection images at the injection distal subclavian artery, showing a successful occlusion of the branch vessel.

Figure 10A:
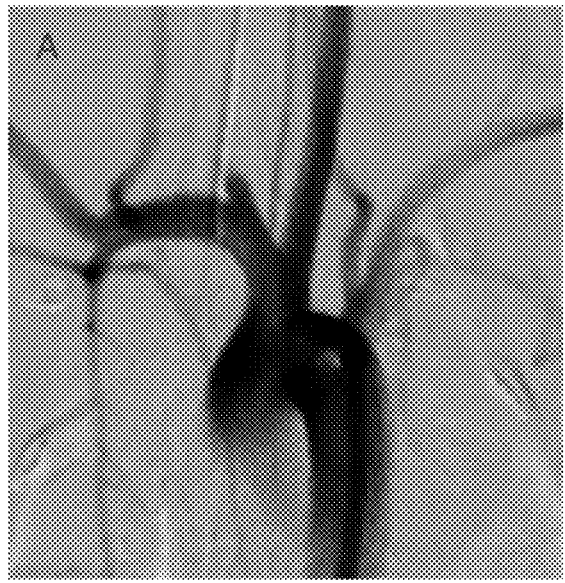
FIGS. 10A, 10B, 10C and 10D demonstrate hydrogel deposition in a rabbit elastase aneurysm model (the aneurysm was created in right common carotid artery by incubating elastase 2 weeks prior to the hydrogel deposition) according to the methods described herein.
Figure 10B:
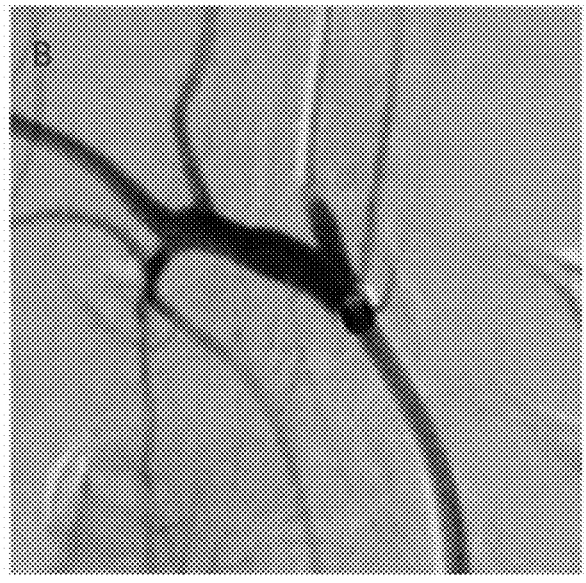
Figure 10C:
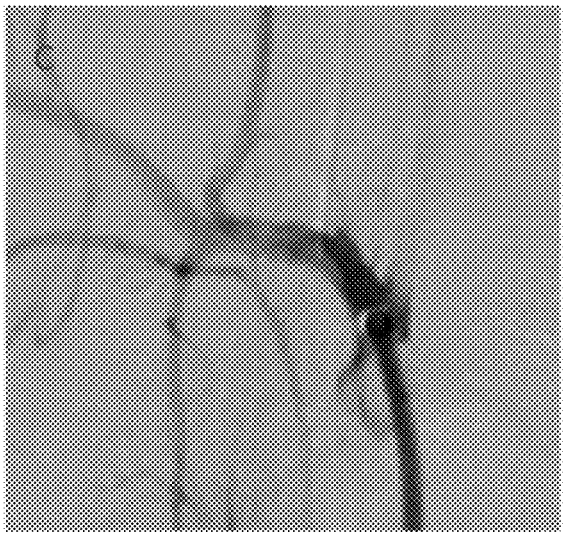
Figure 10D:
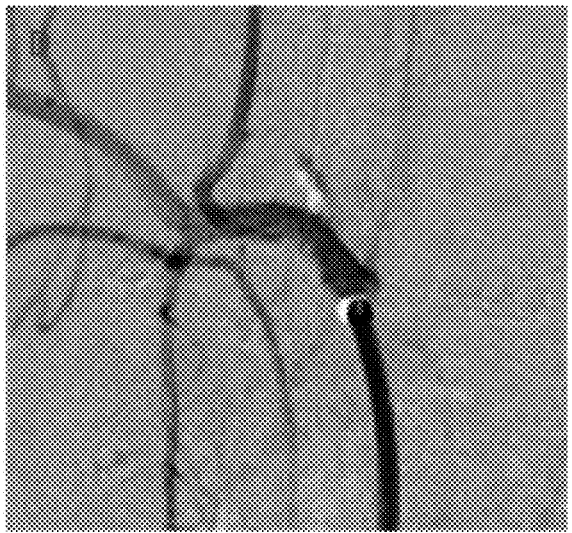

FIGS. 10A-10D demonstrate hydrogel deposition in a rabbit elastase aneurysm model (the aneurysm was created in right common carotid artery by incubating elastase 2 weeks prior to the hydrogel deposition) according to the methods described herein. FIG. 10A shows the aortic arch run showing right common carotid aneurysm. FIG. 10B shows the right subclavian run aneurysm 3.5 mm ×1.6 mm, 1.5 mm neck. FIG. 10C shows the right subclavian run post hydrogel implantation showing 90% occlusion of aneurysm, all distal vessels patent. FIG. 10D shows the right subclavian run showing hydrogel within aneurysm. In this case, an Excelsior® XT27 catheter 2.7 F (0.914 mm distal outer diameter) housing a 200-micron multimodal optical fiber emitting 65 mW/cm$^2$ at 405 nm was used to deliver 2 ml of the hydrogel formulation (15 wt % PEGDA, 4 wt % Laponite XLG nanosilicate platelet, dissolved in Omnipaque 300contrast).

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A system for crosslinking and delivery of a hydrogel precursor within a bodily lumen, the system comprising:
   a catheter;
   flow means operably connectable to a proximal region of said catheter for delivering the hydrogel precursor into said catheter and flowing said hydrogel precursor within said catheter to a distal extrusion port within said catheter;
   a light source capable of emitting incident optical radiation suitable for crosslinking said hydrogel precursor;
   an optical fiber at least partially residing within said catheter, said optical fiber being configured to deliver the incident optical radiation emitted by said light source within said catheter such that said hydrogel precursor is illuminated by the incident optical radiation and is at least partially crosslinked by the incident optical radiation prior to and/or after being extruded through said distal extrusion port;
   wherein said catheter comprises a multilumen region residing within an outer sheath along an elongate portion of the catheter, said flow means being configured to flow the hydrogel precursor through one or more lumens of the multilumen region, and wherein said optical fiber resides, at least in part, within a selected lumen of the multilumen region;
   wherein said catheter comprises a single-lumen distal reaction chamber extending from a distal end of said multilumen region to a distal end of said catheter for partially crosslinking said hydrogel precursor within said catheter before extruding said hydrogel precursor through said distal extrusion port into the bodily lumen; and
   wherein a distal end of said optical fiber is longitudinally positionable within said single-lumen distal reaction chamber for controlling a volume of said hydrogel precursor that is irradiated by the incident optical radiation prior to being extruded through said distal extrusion port.

2. The system according to claim 1 wherein said multilumen region of said catheter comprises a conduit housed within said catheter, said multilumen region thereby comprising (i) an outer lumen formed between an outer sheath of said catheter and said conduit, and (ii) at least one inner lumen defined within said conduit, such that said single-lumen distal reaction chamber extends between a distal end of said multilumen region and said distal end of said catheter.

3. The system according to claim 2 wherein a distal end of said conduit is longitudinally positionable within said catheter for controlling a longitudinal extent of said single-lumen distal reaction chamber.

4. The system according to claim 1 wherein said hydrogel precursor is a first hydrogel precursor and said flow means is a first flow means, and wherein said first flow means is configured to deliver the first hydrogel precursor to a first lumen of said multilumen region, and wherein said system further comprises a second flow means configured to deliver a second fluid to a second lumen of said multilumen region.

5. The system according to claim 4 wherein said first lumen and said second lumen are coaxial.

6. The system according to claim 4 further comprising control and processing circuitry operably connected to said first flow means and said second flow means, said control and processing circuitry comprising at least one processor and associated memory, said memory comprising instructions executable by said at least one processor for performing operations for controlling a flow rate of said first hydrogel precursor and said second fluid.

7. The system according to claim 4 wherein said second fluid is configured to provide a sheath flow around said first hydrogel precursor when said first hydrogel precursor emerges from said multilumen region.

8. The system according to claim 7 wherein said second fluid is a non-crosslinking fluid.

9. The system according to claim 4 wherein said second fluid comprises a second hydrogel precursor.

10. The system according to claim 1 further comprising:
    a detector in optical communication with said optical fiber for detecting optical energy collected from said hydrogel precursor when said hydrogel precursor is illuminated by the incident optical radiation as said hydrogel precursor undergoes at least partial crosslinking; and
    control and processing circuitry operably coupled to said detector and said light source, said control and processing circuitry comprising at least one processor and associated memory, said memory comprising instructions executable by said at least one processor for performing instructions comprising:
    controlling crosslinking of said hydrogel precursor by the incident optical radiation according to feedback generated based on a signal obtained from said detector.

11. The system according to claim 10 wherein said detector is configured to detect reflected optical energy that is responsively reflected by said hydrogel precursor when said hydrogel precursor is illuminated by the incident optical radiation as said hydrogel precursor undergoes at least partial crosslinking.

12. The system according to claim 10 wherein said detector is configured to detect emitted optical energy that is responsively emitted by said hydrogel precursor when said hydrogel precursor is illuminated by the incident optical radiation as said hydrogel precursor undergoes at least partial crosslinking.

13. The system according to claim 12 wherein said detector is configured to detect autofluorescence energy that is responsively emitted by said hydrogel precursor when said hydrogel precursor is illuminated by the incident optical radiation as said hydrogel precursor undergoes at least partial crosslinking.

14. The system according to claim 12 wherein said detector is configured to detect fluorescence energy that is responsively emitted by a fluorescent component of said hydrogel precursor when said hydrogel precursor is illuminated by the incident optical radiation as said hydrogel precursor undergoes at least partial crosslinking.

15. The system according to claim 12 wherein said detector is configured to detect fluorescence energy that is responsively emitted by a fluorescent component of said hydrogel precursor when said hydrogel precursor is illuminated by the incident optical radiation and the fluorescent component reaches a target site within the bodily lumen.

16. The system according to claim 10 wherein said detector is configured to detect one or more spectrally resolved optical signals.

17. The system according to claim 16 wherein said detector comprises a spectrometer.

18. The system according to claim 10 wherein said control and processing circuitry is coupled to said flow means, and wherein said control and processing circuitry is further configured to control said flow means according to the feedback generated based on the signal obtained from said detector.

19. The system according to claim 1 wherein said hydrogel precursor comprises an electrically alignable component capable of undergoing spatial alignment via an electric field, said system further comprising an electric field generator integrated with a distal region of said catheter, said electric field generator being configured to generate an applied electric field suitable for inducing spatial alignment of the electrically alignable component of said hydrogel precursor for generating anisotropy within the at least partially-crosslinked hydrogel precursor.

20. The system according to claim 19 wherein said electric field generator comprises an array of electrodes integrated with said distal region of said catheter.

21. The system according to claim 1 wherein said hydrogel precursor comprises a magnetically alignable component capable of undergoing spatial alignment via a magnetic field, said system further comprising a magnetic field generator integrated with a distal region of said catheter, said magnetic field generator being configured to generate an applied magnetic field suitable for inducing spatial alignment of the magnetically alignable component of said hydrogel precursor within said distal region for generating anisotropy within the at least partially-crosslinked hydrogel precursor.

22. The system according to claim 21 wherein said magnetic field generator comprises a coil integrated with said distal region of said catheter.

23. The system according to claim 1 further comprising an ultrasound generator integrated with a distal region of said catheter, said ultrasound generator being configured to generate an ultrasound field suitable for inducing spatial alignment of an acoustically alignable component of said hydrogel precursor within said distal region for generating anisotropy within the at least partially-crosslinked hydrogel precursor.

24. The system according to claim 23 wherein said ultrasound generator comprises a piezoelectric transducer integrated with said distal region of said catheter.

25. The system according to claim 1 wherein said optical fiber comprises a hydrophobic coating layer.

* * * * *